US009414739B2

(12) United States Patent
Takekoshi et al.

(10) Patent No.: US 9,414,739 B2
(45) Date of Patent: Aug. 16, 2016

(54) IMAGING APPARATUS FOR CONTROLLING FLUORESCENCE IMAGING IN DIVIDED IMAGING SURFACE

(71) Applicant: OLYMPUS CORPORATION, Tokyo (JP)

(72) Inventors: Satoshi Takekoshi, Hachioji (JP); Shunji Takei, Hachioji (JP); Kenji Yamazaki, Hino (JP); Wataru Ono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/641,603

(22) Filed: Mar. 9, 2015

(65) Prior Publication Data

US 2015/0173595 A1     Jun. 25, 2015

Related U.S. Application Data

(63) Continuation of application No. PCT/JP2014/059473, filed on Mar. 31, 2014.

(30) Foreign Application Priority Data

Aug. 1, 2013   (JP) .................................. 2013-160659

(51) Int. Cl.
*A61B 1/04*     (2006.01)
*A61B 1/06*     (2006.01)
(Continued)

(52) U.S. Cl.
CPC ............. *A61B 1/043* (2013.01); *A61B 1/00009* (2013.01); *A61B 1/045* (2013.01); *A61B 1/0638* (2013.01)

(58) Field of Classification Search
CPC ...... A61B 1/043; A61B 1/0009; A61B 1/045; A61B 1/0638
See application file for complete search history.

(56) References Cited

U.S. PATENT DOCUMENTS 6,522,353 B1* 2/2003 Saito ...................... H04N 9/735
                                                  348/223.1
6,529,768 B1* 3/2003 Hakamata .......... A61B 1/00009
                                                  600/310

(Continued)

FOREIGN PATENT DOCUMENTS

JP      2006-061435 A    3/2006
JP      2009-095525 A    5/2009
(Continued)

OTHER PUBLICATIONS

Machine language translation of JP 2006-061435 A, Published Mar. 2006.*

(Continued)

*Primary Examiner* — John P Leubecker
(74) *Attorney, Agent, or Firm* — Scully, Scott, Murphy & Presser, P.C.

(57) ABSTRACT

An imaging apparatus includes: an excitation light emission unit that irradiates a subject with excitation light for exciting a fluorescent substance introduced into the subject; a normal light emission unit that irradiates the subject with normal light including a visible wavelength range different from the excitation light; an imaging unit that forms an optical image of the subject irradiated with the excitation light or normal light on an imaging surface to generate an image signal; a brightness signal generation unit that generates a brightness signal indicating brightness, based on the image signal generated by the imaging unit under irradiation with the normal light; and an amplification unit that sets an amplification factor of the image signal to be generated by the imaging unit under irradiation with the excitation light, based on an amplification factor of the image signal according to the brightness signal generated by the brightness signal generation unit.

8 Claims, 19 Drawing Sheets

(51) Int. Cl.
*A61B 1/00* (2006.01)
*A61B 1/045* (2006.01)

(56) References Cited

U.S. PATENT DOCUMENTS

| | | | |
|---|---|---|---|
| 8,545,399 B2 | 10/2013 | Takei et al. | |
| 8,823,789 B2 | 9/2014 | Ono | |
| 2002/0035330 A1* | 3/2002 | Cline | A61B 1/00009 600/476 |
| 2004/0186351 A1* | 9/2004 | Imaizumi | A61B 1/00009 600/160 |
| 2005/0093886 A1* | 5/2005 | Kubota | H04N 1/3872 345/619 |
| 2006/0020169 A1* | 1/2006 | Sugimoto | A61B 1/00009 600/180 |
| 2006/0055793 A1* | 3/2006 | Adler | A61B 1/045 348/211.99 |
| 2007/0073104 A1* | 3/2007 | Iketani | A61B 1/0005 600/109 |
| 2007/0093691 A1* | 4/2007 | Kobayashi | A61B 1/00009 600/180 |
| 2009/0118578 A1* | 5/2009 | Takasugi | A61B 1/043 600/109 |
| 2010/0204544 A1 | 8/2010 | Takei | |
| 2013/0300849 A1* | 11/2013 | Ono | A61B 1/00006 348/68 |
| 2014/0046131 A1* | 2/2014 | Morita | A61B 1/00179 600/109 |
| 2014/0184769 A1* | 7/2014 | Ishihara | A61B 1/00009 348/68 |

FOREIGN PATENT DOCUMENTS

| | | |
|---|---|---|
| JP | 2009-095566 A | 5/2009 |
| JP | 2009-279172 A | 12/2009 |
| JP | 2011-250925 A | 12/2011 |
| JP | 5200200 B1 | 5/2013 |
| JP | 5245022 B1 | 7/2013 |

OTHER PUBLICATIONS

International Search Report dated Jul. 1, 2014 issued in PCT/JP2014/059473.
English Abstract of WO 2012/172908 A1, dated Dec. 20, 2012.
English Abstract of WO 2013/024788 A1, dated Feb. 21, 2013.
Notice of Allowance dated Dec. 2, 2014 issued in JP 2014-544276.

* cited by examiner (a)

(b)

IMAGING APPARATUS FOR CONTROLLING FLUORESCENCE IMAGING IN DIVIDED IMAGING SURFACE

CROSS-REFERENCE TO RELATED APPLICATIONS

This application is a continuation of PCT international application Ser. No. PCT/JP2014/059473 filed on Mar. 31, 2014 which designates the United States, incorporated herein by reference, and which claims the benefit of priority from Japanese Patent Application No. 2013-160659, filed on Aug. 1, 2013, incorporated herein by reference.

BACKGROUND

1. Technical Field

The disclosure relates to an imaging apparatus that irradiates a subject with excitation light or visible light and receives reflected light from the subject by a plurality of pixels to perform photoelectric conversion, to thereby output image information.

2. Related Art

Conventionally, in medical fields, an endoscope system is used for observing an interior of an organ of a subject. In general, the endoscope system, which is a kind of an imaging apparatus, inserts an elongated and flexible insertion section into a body cavity of a subject such as a patient, and irradiates body tissues in the body cavity with white light through the inserted insertion section and receives reflected light by an imaging unit provided at a distal end of the insertion section, to thereby capture an in-vivo image. An image signal of the biological image taken by the endoscope system is transmitted to an image processing device outside the subject body through a transmission cable inside the insertion section and subjected to image processing in the image processing device and is, thereby, displayed on a monitor of the endoscope system. A user such as a doctor observes the interior of the organ of the subject through the in-vivo image displayed on the monitor.

As such an endoscope system, there is known technology capable of performing fluorescence observation that irradiates body tissues into which a fluorescence agent including a fluorescence marker is introduced with excitation light of a specific wavelength to capture fluorescence light or normal observation that irradiates body tissues with normal light in a visible wavelength range to capture reflected light (see Japanese Laid-open Patent Publication No. 2006-61435). In this technology, a brightness level of a fluorescence image is automatically adjusted with a brightness level of an image captured using the normal light set as a target value, whereby it is possible to display the fluorescence image with proper brightness without imposing burden on a user.

SUMMARY

In some embodiments, an imaging apparatus includes: an excitation light emission unit configured to irradiate a subject with excitation light for exciting a fluorescent substance introduced into the subject; a normal light emission unit configured to irradiate the subject with normal light including a visible wavelength range different from the excitation light; an imaging unit configured to form an optical image of the subject irradiated with the excitation light or normal light on an imaging surface to generate an image signal; a brightness signal generation unit configured to generate a brightness signal indicating brightness, based on the image signal generated by the imaging unit under irradiation with the normal light; and an amplification unit configured to set an amplification factor of the image signal to be generated by the imaging unit under irradiation with the excitation light, based on an amplification factor of the image signal according to the brightness signal generated by the brightness signal generation unit.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, a medical endoscope system that captures and display an image of an interior of a body cavity of a subject such as a patient will be described as modes for carrying out the invention (hereinafter, referred to as "embodiments"). The embodiments do not limit the invention. The same reference signs are used to designate the same elements throughout the drawings. Further, it is noted that each drawing is a schematic diagram, and a relationship between a thickness and a width, a dimensional ratio of each member, and the like may differ from those of actual ones. Furthermore, different drawings include elements which have different dimensional relations and ratios.

First Embodiment

Figure 1:
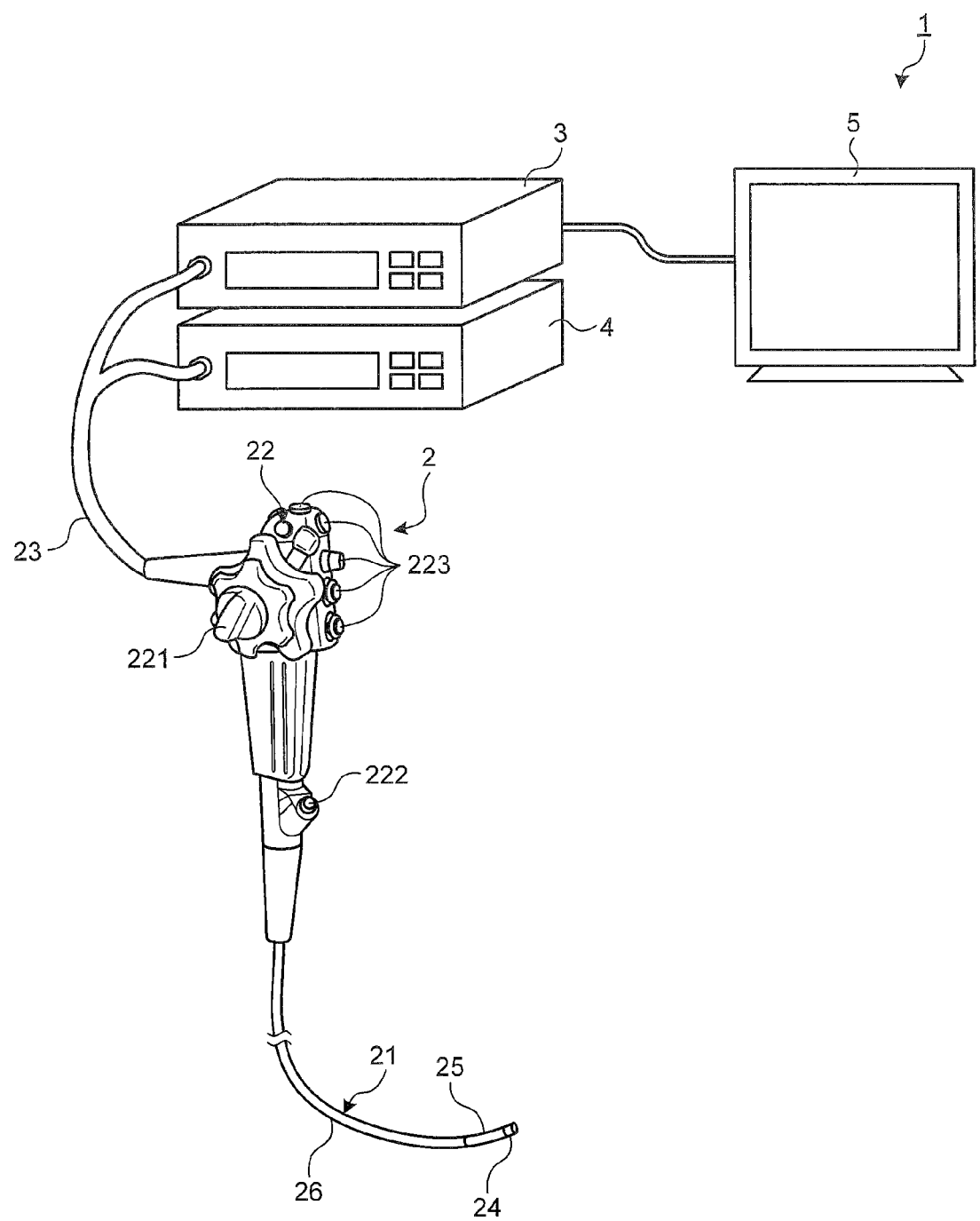
FIG. 1 is a view illustrating a schematic configuration of an endoscope system as an imaging apparatus according to a first embodiment of the present invention.

FIG. 1 is a view illustrating a schematic configuration of the endoscope system as an imaging apparatus according to a first embodiment of the present invention. As illustrated in FIG. 1, an endoscope system 1 includes an endoscope 2 whose distal end is inserted into a body cavity of a subject to capture an in-vivo image of the subject, a control device 3 that performs specified processing on the in-vivo image captured by the endoscope 2 and totally controls operation of the endoscope system 1, a light source device 4 serving as a light source unit for generating illumination light or excitation light to be emitted from the distal end of the endoscope 2, and a display device 5 that displays the in-vivo image obtained as a result of the image processing applied by the control device 3.

The endoscope 2 includes an elongated and flexible insertion section 21, an operating unit 22 connected to a proximal end side of the insertion section 21 and configured to receive an input of various operation signals, and a universal cord 23 extending in a direction different from a direction in which the insertion section 21 extends from the operating unit 22 and incorporating various cables connected to the control device 3 and light source device 4.

The insertion section 21 includes a distal end section 24 incorporating an imaging element to be described later, a freely bendable bending portion 25 constituted by a plurality of bending pieces, and a long flexible tube portion 26 connected to a proximal end side of the bending portion 25.

Figure 2:
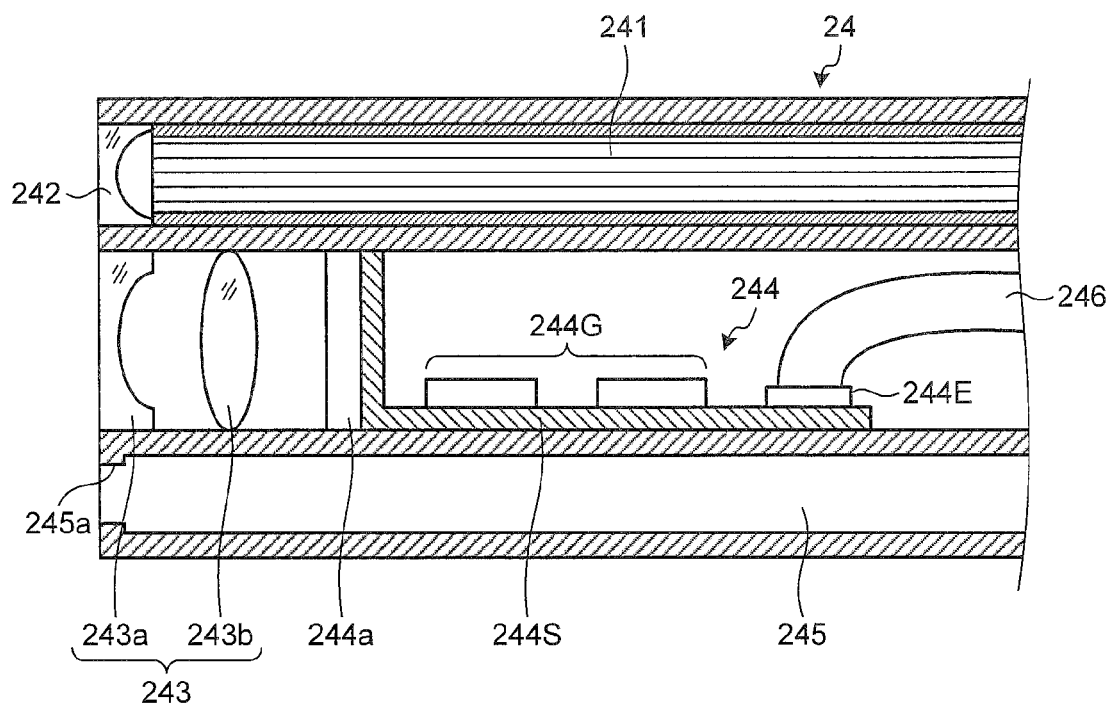
FIG. 2 is a cross-sectional view schematically explaining an internal configuration of a distal end section of an endoscope illustrated in FIG. 1.

FIG. 2 is a cross-sectional view schematically explaining an internal configuration of the distal end section 24. As illustrated in FIG. 2, the distal end section 24 includes a light guide 241 constituted using glass fiber or the like and serving as a light guide for light generated by the light source device 4, an illumination lens 242 provided at a distal end of the light guide 241, an optical system 243 for light collection, an imaging element 244 provided at an image forming position of the optical system 243 and configured to receive light collected by the optical system 243, perform photoelectric conversion to convert it into an electric signal, and apply specified signal processing to the obtained electric signal, and a treatment tool channel 245 through which a treatment tool for the endoscope 2 is passed.

The optical system 243 includes at least a lens 243a and a lens 243b. A type or the number of lenses constituting the optical system 243 is not limited to that illustrated in FIG. 2.

Figure 3A:
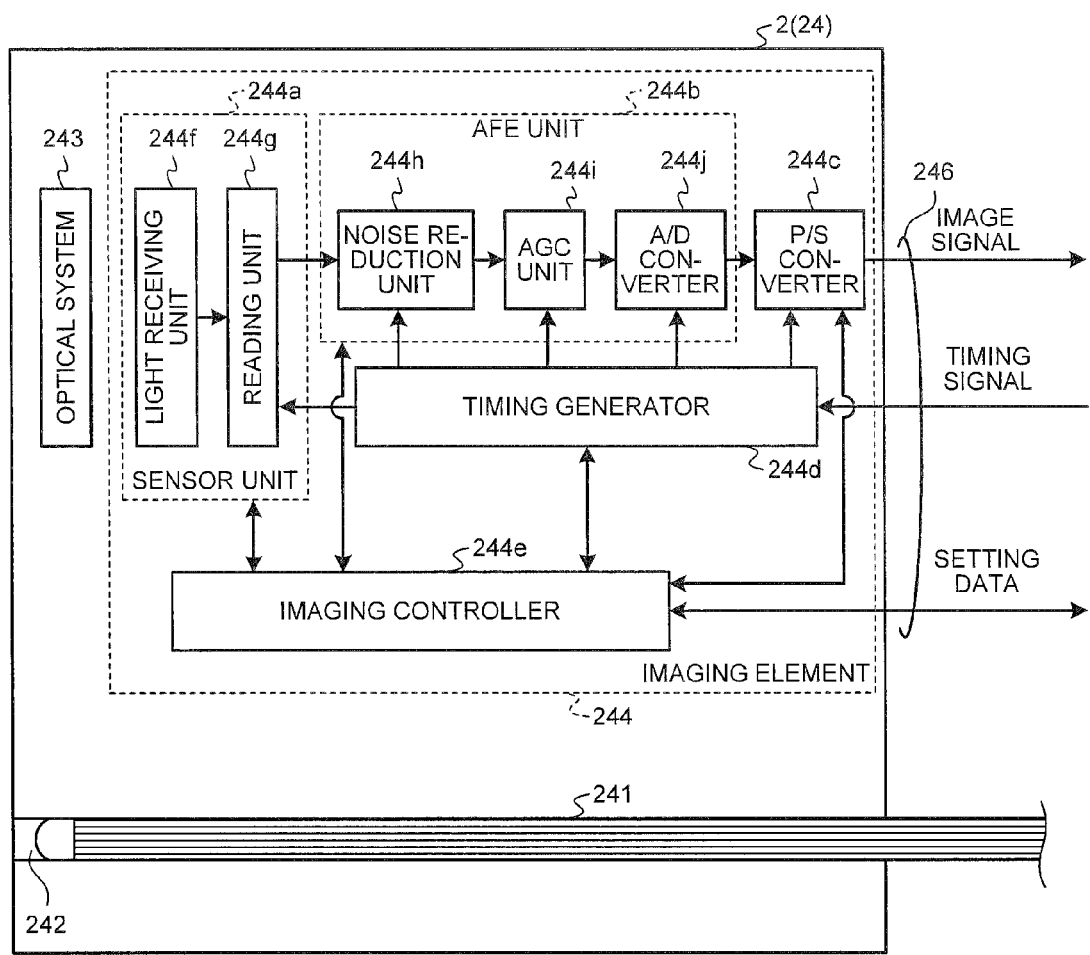
FIGS. 3A and 3B are a block diagram illustrating a functional configuration of a main part of the endoscope system according to the first embodiment of the present invention.
Figure 3B:
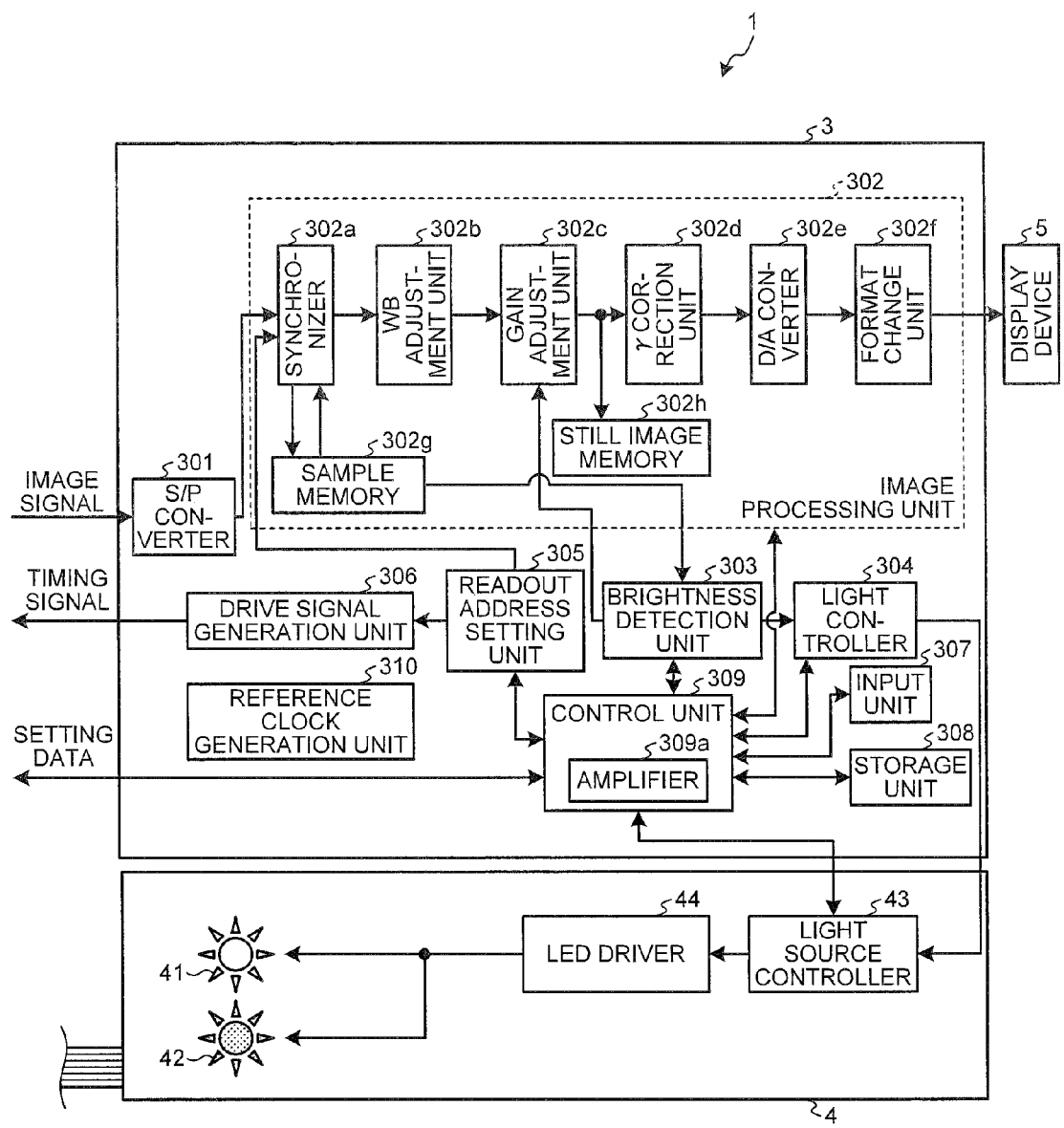

FIGS. 3A and 3B are a block diagram illustrating a functional configuration of a main part of the endoscope system 1. A configuration of the imaging element 244 will be described with reference to FIGS. 3A and 3B. As illustrated in FIGS. 3A and 3B, the imaging element 244 includes a sensor unit 244a that photoelectric converts light from the optical system 243 to output an electric signal, an analog front end 244b (hereinafter, referred to as "AFE unit 244b") that applies noise reduction and A/D conversion to the electric signal output from the sensor unit 244a, a P/S converter 244c that parallel/serial converts a digital signal output from the AFE unit 244b, a timing generator 244d that generates driving timing of the sensor unit 244a and pulses for various signal processing performed in the AFE unit 244b and P/S converter 244c, and an imaging controller 244e that controls operation of the imaging element 244. The imaging element 244 is a complementary metal oxide semiconductor (CMOS) image sensor.

The sensor unit 244a is connected to an IC circuit group 244G through a substrate 244S. The IC circuit group 244G includes a plurality of IC circuits having functions corresponding respectively to the AFE unit 244b, the P/S converter 244c, the timing generator 244d, and the imaging controller 244e.

The sensor unit 244a includes a light receiving unit 244f in which a plurality of pixels each having a photodiode that accumulates electric charge in accordance with a light amount and an amplifier that amplifies the electric charge accumulated by the photodiode are arranged in two-dimensional matrix form and a reading unit 244g that reads, as image information, an electric signal generated by a pixel arbitrarily set as a readout target from among the plurality of pixels in the light receiving unit 244f. In the light receiving unit 244f, a color filter for each of RGB is provided for each pixel, enabling acquisition of a color image.

The AFE unit 244b includes a noise reduction unit 244h that reduces a noise component included in an electric signal (analog), an auto gain control (AGC) unit 244i that maintains a constant output level by adjusting an amplification factor (gain) of the electric signal, and an A/D converter 244j that applies A/D conversion to the electric signal output through the AGC unit 244i. The noise reduction unit 244h performs noise reduction by using, for example, a correlated double sampling method.

The imaging controller 244e controls various operations of the distal end section 24 according to setting data received from the control device 3. The imaging controller 244e is configured by using a central processing unit (CPU) and the like. Further, the imaging controller 244e sets a readout region that the reading unit 244g reads from the light receiving unit 244f according to the setting data received from the control device 3.

An electrode 244E provided on the substrate 244S is connected with a cable assembly 246 in which a plurality of signal lines through which an electric signal is exchanged between the electrode 244E and control device 3 are bundled. The plurality of signal lines include a signal line that transmits the image signal output from the imaging element 244 to the control device 3, a signal line that transmits a control signal output from the control device 3 to the imaging element 244, and the like.

The operating unit 22 includes a bending knob 221 that bends the bending portion 25 in up/down and left/right directions, a treatment tool insertion section 222 that inserts a treatment tool such as a biological forceps, a laser knife, and a test probe into a body cavity, and a plurality of switches 223 as an operation input section that inputs an operation command signal for peripheral equipment such as an air supply unit, a water supply unit, and a gas supply unit in addition to the control device 3 and the light source device 4. The treatment tool inserted from the treatment tool insertion section 222 is extracted from an opening 245a through the treatment tool channel 245 of the distal end section 24.

The universal cord 23 includes at least the light guide 241 and cable assembly 246. The light guide 241 of the universal cord 23 is connected to the light source device 4. The cable assembly 246 of the universal cord 23 is connected to the control device 3.

Reference will be made below to a configuration of the control device 3. The control device 3 includes an S/P converter 301, an image processing unit 302, a brightness detection unit 303, a light controller 304, a readout address setting unit 305, a drive signal generation unit 306, an input unit 307, a storage unit 308, a control unit 309, and a reference clock generation unit 310.

The S/P converter 301 applies serial/parallel conversion to the image signal (digital signal) received from the distal end section 24.

The image processing unit 302 generates an in-vivo image to be displayed by the display device 5 based on the image signal of a parallel form output from the S/P converter 301. The image processing unit 302 includes a synchronizer 302a, a white balance (WB) adjustment unit 302b, a gain adjustment unit 302c, a γ correction unit 302d, a D/A converter 302e, a format change unit 302f, and a sample memory 302g and a still image memory 302h.

The synchronizer 302a inputs the image signal input as pixel information in three memories (not illustrated) provided for each pixel, sequentially updates and retains the values of the memories in association with the addresses of pixels of the light receiving unit 244f read by the reading unit 244g, and synchronizes the image signals of the three memories as RGB image signals. The synchronizer 302a sequentially outputs the synchronized RGB image signals to the white balance adjustment unit 302b and outputs some RGB image signals as signals for image analysis such as brightness detection to the sample memory 302g.

The white balance adjustment unit 302b automatically adjusts white balance of the RGB image signal. More specifically, the white balance adjustment unit 302b automatically adjusts the white balance of the RGB image signal based on a color temperature included in the RGB image signal.

The gain adjustment unit 302c adjusts a gain of the RGB image signal. The gain adjustment unit 302c outputs the RGB signal that has been subjected to the gain adjustment to the γ correction unit 302d and outputs some RGB signals as a signal for displaying a still image, a signal for displaying an enlarged image, or a signal for displaying an emphasized image to the still image memory 302h.

The γ correction unit 302d performs gradation correction (γ correction) of the RGB image signal corresponding to the display device 5.

The D/A converter 302e converts the RGB image signal that has been subjected to the gradation correction, which is output by the γ correction unit 302d, into an analog signal.

The format change unit 302f converts the image signal converted into an analog signal into a moving image file format such as a high vision format and outputs the converted image signal to the display device 5.

The brightness detection unit 303 detects a brightness level corresponding to each pixel from the RGB image signal retained by the sample memory 302g to record the detected brightness level in a memory provided inside the brightness detection unit 303 and to output the detected brightness level to the control unit 309. In addition, the brightness detection unit 303 calculates an adjusted gain value and an amount of irradiation light based on the detected brightness level to output the adjusted gain value to the gain adjustment unit 302c and to output the amount of irradiation light to the light controller 304. Further, the brightness detection unit 303 generates, based on the image signal generated by the imaging element 244 of the endoscope 2, a brightness signal indicating the brightness and outputs the brightness signal to the control unit 309. In the first embodiment, the brightness detection unit 303 functions as a brightness signal generation unit.

Under control of the control unit 309, the light controller 304 sets a type, an amount, an emitting timing, and the like of the light generated by the light source device 4 based on the amount of irradiation light calculated by the brightness detection unit 303 and transmits a light source synchronization signal including the set conditions to the light source device 4.

The readout address setting unit 305 has a function of setting pixels as reading targets and a reading order on a light receiving surface of the sensor unit 244a. That is, the readout address setting unit 305 has a function of setting addresses of the pixels of the sensor unit 244a to be read by the AFE unit 244b. In addition, the readout address setting unit 305 outputs set address information of the pixels as reading targets to the synchronizer 302a.

The drive signal generation unit 306 generates a timing signal for driving the imaging element 244 and transmits the timing signal to the timing generator 244d through a specified signal line included in the cable assembly 246. The timing signal includes address information of the pixels as reading targets.

The input unit 307 accepts an input of various signals such as an operation command signal that indicates operation of the endoscope system 1.

The storage unit 308 is realized by using a semiconductor memory such as a flash memory or a dynamic random access memory (DRAM). The storage unit 308 stores therein various programs for operating the endoscope system 1 and data including various parameters and the like required for operation of the endoscope system 1.

The control unit 309 is configured by using a CPU and the like. The control unit 309 performs drive control of components including the distal end section 24 and the light source device 4 and performs input and output control of information for the components. The control unit 309 transmits setting data for imaging control to the imaging controller 244e through a specified signal line included in the cable assembly 246. The setting data includes: indicating information indicating an imaging speed (frame rate) of the imaging element 244 and a readout speed of the pixel information from arbitrary pixels of the sensor unit 244a; transmission control information of the pixel information that the AFE unit 244b reads; and the like. The control unit 309 includes an amplifier 309a.

The amplifier 309a sets an amplification factor of the image signal that the imaging element 244 generates under irradiation with excitation light based on an amplification factor according to the brightness signal input from the brightness detection unit 303. Specifically, the amplifier 309a sets, in the AGC unit 244i, an amplification factor (gain) of the image signal that the imaging element 244 generates under irradiation with excitation light based on an amplification factor set in the AGC unit 244i according to the brightness signal that the brightness detection unit 303 generates based on the image signal that the imaging element 244 generates under irradiation with normal light (visible light).

The reference clock generation unit 310 generates a reference clock signal as a reference of operations of the components of the endoscope system 1 and supplies the generated reference clock signal to the components of the endoscope system 1.

Reference will be made below to a configuration of the light source device 4. The light source device 4 includes a white-light light source 41, a special-light light source 42, a light source controller 43, and a light emitting diode (LED) driver 44.

The white-light light source 41 is a white LED and generates white illumination light under control of the light source controller 43.

The special-light light source 42 generates excitation light for exciting a fluorescent substance introduced into a subject. Specifically, the special-light light source 42 generates infrared light. Further, the special-light light source 42 may generate, as the special light, one of R-, G-, and B-component lights, each of which is a light different in wavelength band from the white illumination light and has been band-narrowed by a narrow band-pass filter. The special light that the special-light light source 42 generates may include narrow band imaging (NBI) illumination light of two kinds of bands, which are blue light and green light that have been band-narrowed so as to be easily absorbable by hemoglobin in blood.

The light source controller 43 controls an amount of current supplied to the white-light light source 41 or special-light light source 42 according to light source synchronization signal transmitted from the light controller 304.

The LED driver 44 supplies current to the white-light light source 41 or special-light light source 42 under control of the light source controller 43 to make the white-light light source 41 or special-light light source 42 generate excitation light. The light generated by the white-light light source 41 or special-light light source 42 travels through the light guide 241 and is emitted outside from a distal end of the distal end section 24.

The display device 5 has a function of receiving the in-vivo image generated by the control device 3 from the control device 3 through a video cable and displaying the in-vivo image. The display device 5 is provided with a liquid crystal display or an organic electro luminescence (EL) display.

Figure 4:
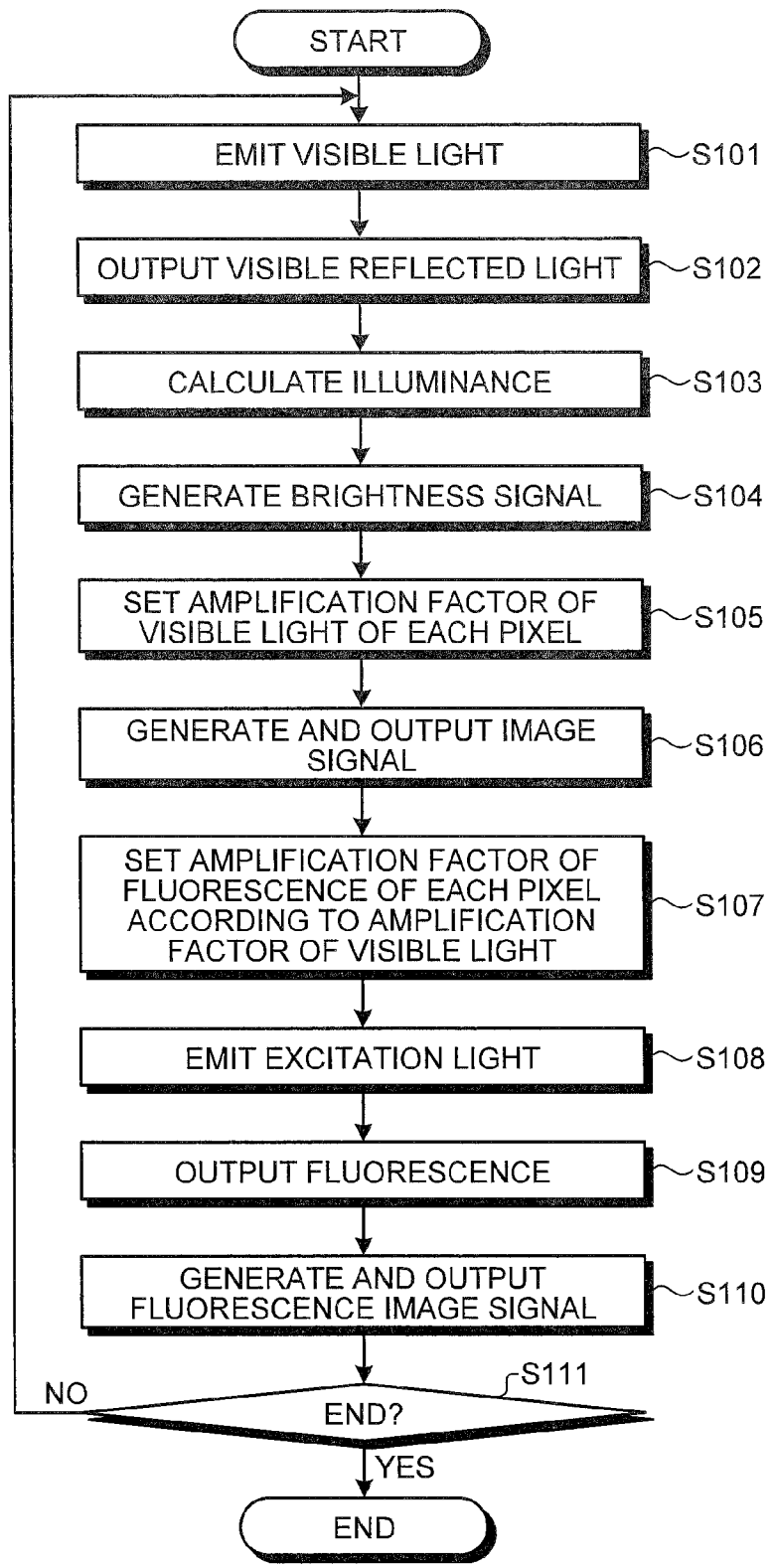
FIG. 4 is a flowchart illustrating an outline of processing that the endoscope system according to the first embodiment of the present invention executes.

Reference will be made below to processing to be executed for fluorescence observation of a subject in the thus configured endoscope system 1. FIG. 4 is a flowchart illustrating an outline of processing that the endoscope system 1 executes. In the following description, it is assumed that a fluorescence agent including a fluorescence marker has already been introduced into a living body of the subject by an operator using the treatment tool.

As illustrated in FIG. 4, the light source controller 43 drives the LED driver 44 under control of the control unit 309 to make the white-light light source 41 emit visible light (step S101).

Subsequently, the imaging controller 244e drives the reading unit 244g at a given timing under control of the control unit 309 to output an image signal of visible reflected light received by the light receiving unit 244f to the control device 3 (step S102).

Thereafter, the brightness detection unit 303 acquires the image signal of the visible light from the sample memory 302g and calculates an illuminance of each image in the light receiving unit 244f (step S103), thereby generating a brightness signal of each pixel (step S104).

Subsequently, based on the brightness signal generated by the brightness detection unit 303, the amplifier 309a sets, in the AGC unit 244i of the AFE unit 244b through the imaging controller 244e, an amplification factor of an image signal of visible light (normal light) output from each pixel of the light receiving unit 244f (step S105).

Thereafter, the control unit 309 causes the image processing unit 302 to generate an image signal of while light and output the white light image signal to the display device 5 (step S106). Specifically, when a normal observation mode based on the white light is set in the endoscope system 1, the control unit 309 causes the image processing unit 302 to output the white light image signal to the display device 5. This allows the operator to confirm the image displayed on the display device 5 and thereby to perform the normal observation of the subject. Further, the control unit 309 may make the image processing unit 302 store the white light image signal in the storage unit 308.

Subsequently, according to the amplification factor of the visible light, the amplifier 309a sets, in the AGC unit 244i of the AFE unit 244b through the imaging controller 244e, an amplification factor of a fluorescence image signal output from each image in the light receiving unit 244f (step S107).

Thereafter, under control of the control unit 309, the light source controller 43 drives the LED driver 44 to make the special-light light source 42 to emit excitation light (step S108).

Subsequently, under control of the control unit 309, the imaging controller 244e drives the reading unit 244g at a given timing to output the fluorescence image signal received by the light receiving unit 244f to the control device 3 (step S109).

Thereafter, the control unit 309 causes the image processing unit 302 to generate the fluorescence image signal and output the generated fluorescence image signal to the display device 5 (step S110). This allows the operator to confirm the fluorescence image displayed on the display device 5 and thereby to perform the fluorescence observation inside the subject.

Subsequently, the control unit 309 determines whether or not an instruction signal instructing end of the observation of the subject has been input from the input unit 307 (step S111). When the control unit 309 determines that the instruction signal has been input (Yes in S111), the endoscope system 1 ends this routine. On the other hand, when the control unit 309 determines that the instruction signal has not been input through the input unit 307 (No in S111), the endoscope system 1 returns to step S101.

According to the first embodiment described above, the amplifier 309a sets the amplification factor of the fluorescence of each pixel based on the amplification factor of each image in the light receiving unit 244f according to the brightness signal of the image signal that the imaging element 244 generates under irradiation with the white light generated by the brightness detection unit 303. This prevents a change in fluorescence intensity due to light distribution or influence of light absorption characteristics of an organ, thereby allowing the display device 5 to display a clear fluorescence image of the subject.

Further, according to the first embodiment, a region where reflected light obtained by irradiating body tissues with visible light is weak (i.e., dark region or bleeding region) is considered to be a region (location) where illumination light does not reach due to a long distance from the distal end section 24 or inadequate light distribution, and the same is applied to the excitation light. Thus, as described above, based on the amplification factor of each image in the light receiving unit 244f according to the brightness signal of the image signal that the imaging element 244 generates under irradiation with the white light generated by the brightness detection unit 303, the amplifier 309a sets the amplification factor of the fluorescence of each pixel. As a result, it is possible to adequately perform observation of the fluorescence image without overlooking a fluorescence agent accumulation region.

Further, according to the first embodiment, even when agents having the same accumulation degree are observed, or even when a difference between intensity of the excitation light caused due to a distance from the distal end section 24 to the body tissues and intensity of the acquired fluorescence and a difference in optical characteristics among tissues surrounding the agent accumulation region are caused, the amplifier 309a optimizes an image-taking sensitivity with respect to each pixel such that a ratio between the amplification factor of the reflected light from the surrounding organ and amplification factor of the fluorescence is constant, thereby allowing observation of the fluorescence image to be adequately performed. In place of making the ratio constant, the amplifier 309a may multiply the amplification factor of the reflected light by a constant coefficient.

Further, in the first embodiment, the amplifier 309a sets the amplification factor of the fluorescence according to the amplification factor of the white light (visible light); alternatively, for example, when the fluorescence is infrared-ray (IR) light, a brightness signal corresponding to an image signal of red (R) included in the image signal may be used to set the amplification factor, followed by setting of the amplification factor of the fluorescence according to the set amplification factor. This reduces processing load of the control unit 309 to thereby increase a frame rate with which the endoscope 2 performs imaging operation.

Second Embodiment

Reference will be made below to a second embodiment of the present invention. An endoscope system according to the second embodiment only differs from the first embodiment in the configurations of the control unit of the control device and processing to be executed by the endoscope system. Specifically, in the above first embodiment, the amplification factor of each image is set upon the fluorescence observation; on the other hand, in the second embodiment, a region of the light receiving unit is divided into a plurality of regions, and the amplification factor upon the fluorescence observation is set for each divided region. Thus, hereinafter, a configuration of the control unit of the endoscope system according to the second embodiment is described first, followed by processing to be executed by the endoscope system. In the second embodiment, the same reference signs are given to the same elements as in the first embodiment.

Figure 5A:
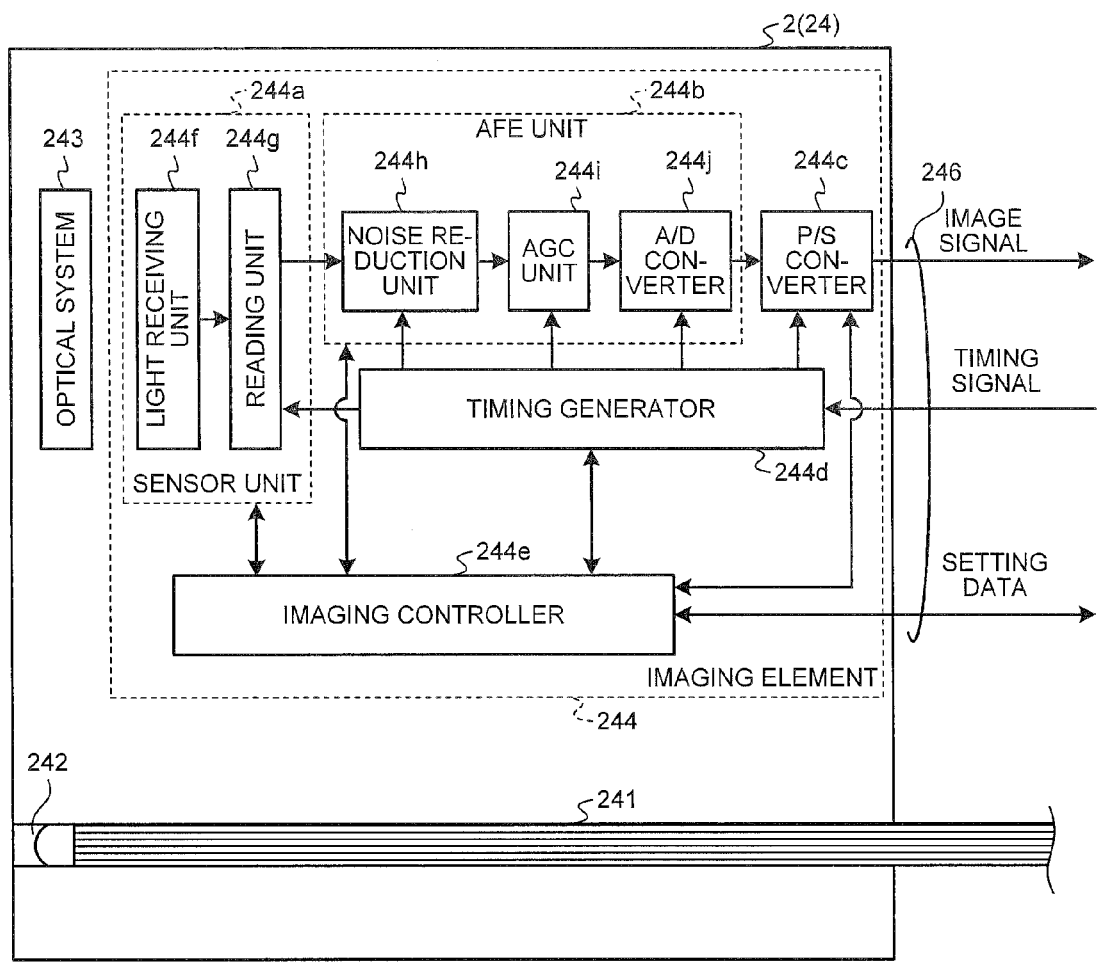
FIGS. 5A and 5B are a block diagram illustrating a functional configuration of a main part of an endoscope system according to a second embodiment of the present invention.
Figure 5B:
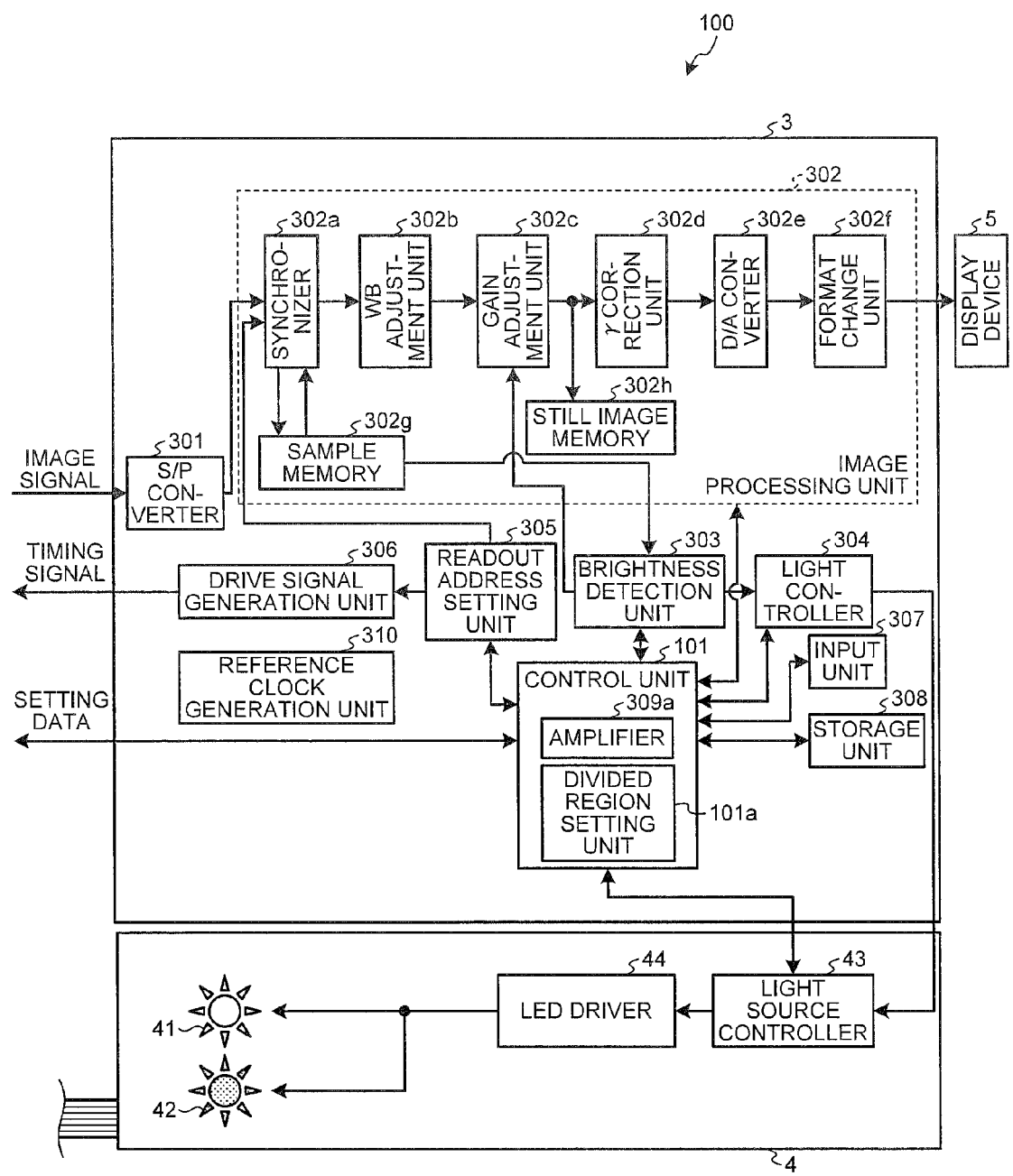

FIGS. 5A and 5B are a block diagram illustrating a functional configuration of a main part of an endoscope system 100 according to the second embodiment. As illustrated in FIG. 5B, a control device 3 of the endoscope system 100 includes a control unit 101.

The control unit 101 is configured by using a CPU and the like and performs drive control of components including the distal end section 24 and the light source device 4 and input and output control of information for the components. The control unit 101 transmits setting data for imaging control to the imaging controller 244e through a specified signal line included in the cable assembly 246. The control unit 101 includes an amplifier 309a and a divided region setting unit 101a.

The divided region setting unit 101a divides an imaging surface of the sensor unit 244a into specified regions to set a plurality of divided regions. Specifically, the divided region setting unit 101a divides the imaging surface of the sensor unit 244a through the readout address setting unit 305 to set a plurality of divided regions. The plurality of divided regions are used when the amplifier 309a to be described later sets the amplification factor in each divided region for the fluorescence observation.

Reference will be made below to processing to be executed by the endoscope system 100 having the above configuration.

Figure 6:
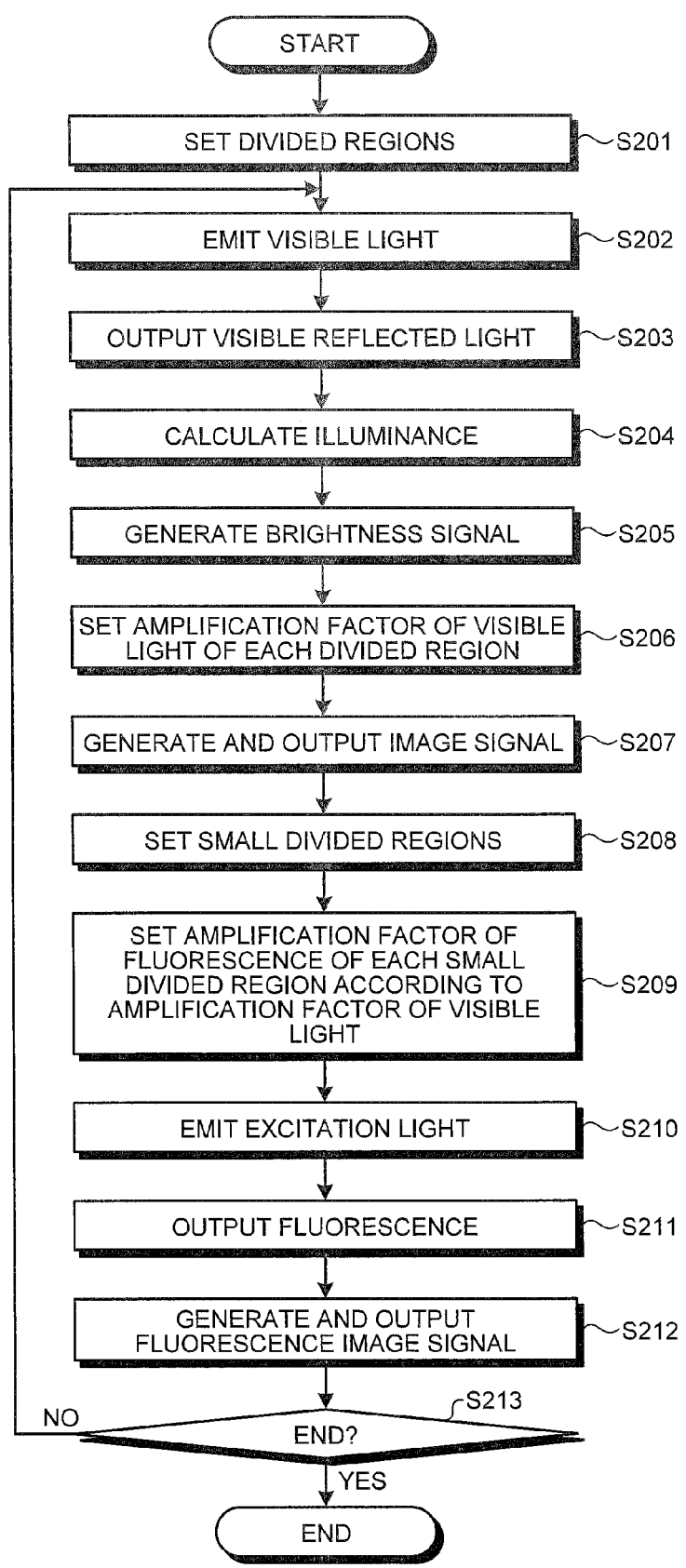
FIG. 6 is a flowchart illustrating an outline of processing that the endoscope system according to the second embodiment of the present invention executes.

FIG. 6 is a flowchart illustrating an outline of processing that the endoscope system 100 according to the second embodiment executes.

Figure 7:
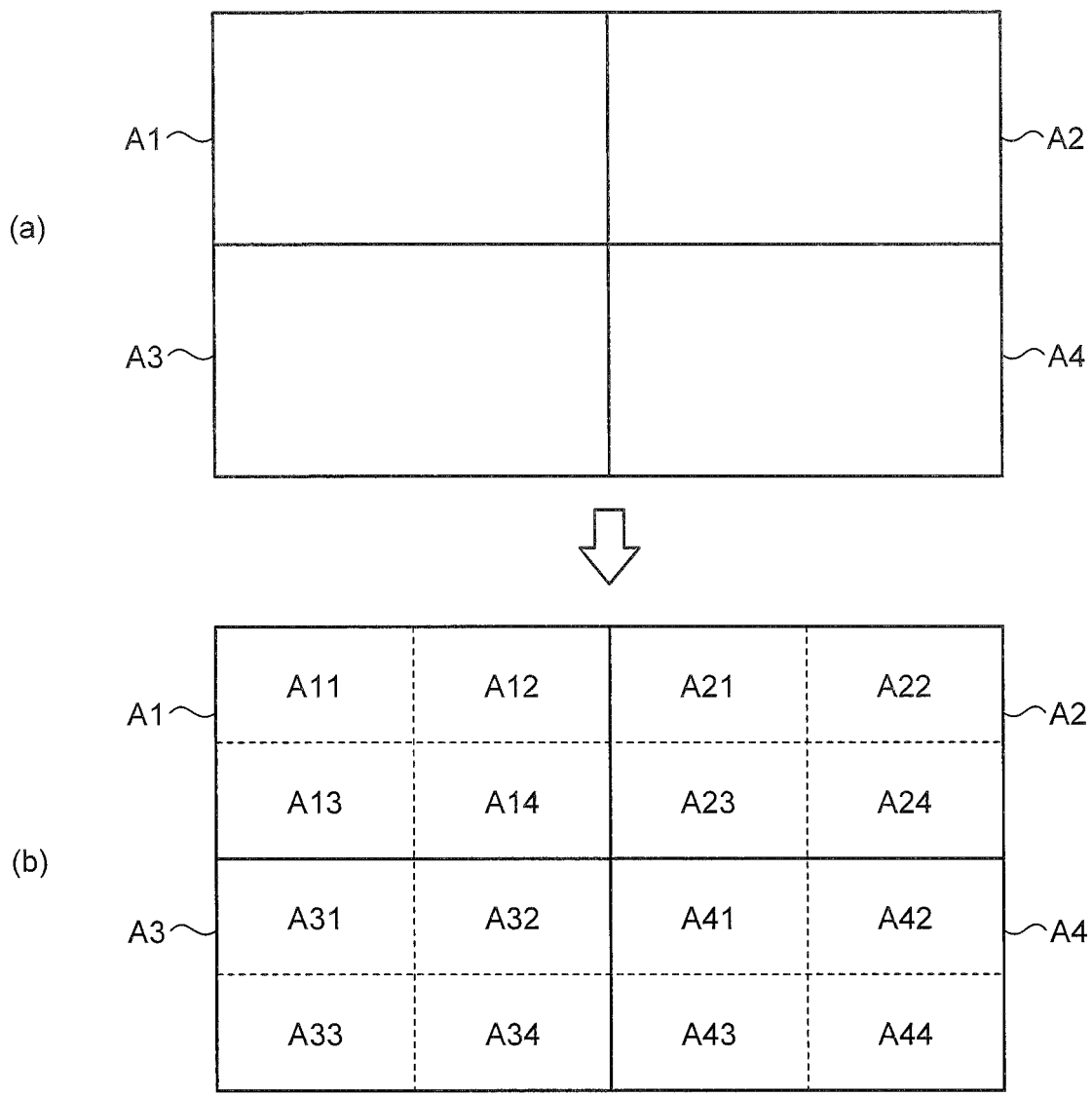
FIG. 7 is a view schematically illustrating divided regions obtained by division of an imaging surface performed by a divided region setting unit of FIG. 5B.

As illustrated in FIG. 6, the divided region setting unit 101a divides, through the imaging controller 244e, a region of the light receiving unit 244f from which the reading unit 244g reads the image signal to set the divided regions (step S201). For example, as illustrated in (a) of FIG. 7, the divided region setting unit 101a divides a light receiving surface of the sensor unit 244a by four to set divided regions A1 to A4.

Steps S202 and S203 correspond respectively to steps S101 and S102 of above-mentioned FIG. 4.

Subsequently, the brightness detection unit 303 acquires the image signal of visible light from the sample memory 302g, calculates an illuminance of each divided region of the light receiving unit 244f (step S204), and generates a brightness signal of each divided region (step S205). Specifically, as illustrated in (a) of FIG. 7, the brightness detection unit 303 calculates the illuminances of the respective divided regions A1 to A4 set by the divided region setting unit 101a and generates the brightness signals of the respective divided regions A1 to A4.

Thereafter, based on the brightness signal of each divided region detected by the brightness detection unit 303, the amplifier 309a sets, in the AGC unit 244i of the AFE unit 244b through the imaging controller 244e, the amplification factor of visible light of the image signal output from each divided region of the light receiving unit 244f (step S206).

Subsequently, the control unit 101 causes the image processing unit 302 to generate the image signal of the white light and output the generated image signal to the display device 5 (step S207).

Thereafter, the divided region setting unit 101a further divides each divided region of the visible light to set small divided regions (step S208). For example, as illustrated in (b) of FIG. 7, the divided region setting unit 101a further divides the divided region A1 of the visible light to set small divided regions A11 to A14 of the excitation light.

Subsequently, the amplifier 309a sets the amplification factor of the fluorescence of each small divided region according to the amplification factor of each divided region of the visible light (step S209). Specifically, the amplifier 309a sets the amplification factor of the fluorescence of the small divided regions A11 to A14 according to the amplification factor of the divided region A1. In this case, the amplifier 309a sets the amplification factor of the fluorescence of the small divided regions A11 to A14 based on an average value of the brightness signals of the respective pixels in the divided region A1. Thus, it is possible to set, in the divided regions A1 to A4, an average value of intensities of reflected light of the visible light caused based on a distance from the endoscope 2 to an intra-body surface of the subject or optical characteristics of an organ and thereby to adjust a gain for making constant a brightness ratio between the average value and fluorescence in the small divided regions A11 to A14, A21 to A24, A31 to A34, and A41 to A44.

Steps S210 to S213 correspond respectively to steps S108 and S111 of FIG. 4.

According to the second embodiment described above, the amplifier 309a sets, for the divided regions set by the divided region setting unit 101a, the amplification factor of the image signal that the imaging element 244 generates under irradiation with the excitation light. Thus, it is possible to set, in the divided regions, the average value of intensities of reflected light of the visible light caused based on a distance from the endoscope 2 to an intra-body surface of the subject or optical characteristics of an organ and thereby to adjust a gain for making constant a brightness ratio between the average value and fluorescence in the divided regions.

Further, according to the second embodiment, the divided region setting unit 101a further divides each divided region of the imaging surface of the sensor unit 244a to set the small divided regions, and the amplifier 309a sets the amplification factor of the image signal of the fluorescence corresponding to each small divided region, so that it is possible to adjust the gain of the fluorescence more finely. Thus, even when a distance between the distal end section 24 and body tissues is changed in the range of capturing, it is possible to adequately and evenly amplify the image signal on the imaging surface of the imaging element 244, thereby allowing a smooth fluorescence image to be captured.

Further, according to the second embodiment, it is possible to obtain an image in which the fluorescence image emitted by irradiation of the excitation light is superimposed on the visible light (white light) image with a sufficient dynamic range or contrast even for a subject having a light distribution or an absorption distribution of the image.

In the second embodiment, the amplifier 309a sets the amplification factor of the image signal of the fluorescence corresponding to each divided region according to the amplification factor of the visible light; however, it is not necessary to set amplification factor for a divided region with a specified fluorescence intensity or more. This makes a surrounding region of the fluorescence corresponding to an affected part easy to see and reduces noise caused due to the amplification.

Further, in the second embodiment, the amplification factor of the image signal upon the fluorescence observation is set by adjusting the gain in the AGC unit 244i. Alternatively, however, it is possible to adjust sensitivity or amplification factor by multiple readout without resetting each pixel of the sensor unit 244a.

Further, in the second embodiment, the divided region setting unit 101a divides the imaging surface of the sensor unit 244a by four; however, the number of divisions may be set arbitrarily according to need. For example, the divided region setting unit 101a may divide the imaging surface of the sensor unit 244a into specified divided regions, e.g., nine divided regions according to a size of the imaging surface of the sensor unit 244a or depending on organ or site of the subject. Similarly, the divided region setting unit 101a may arbitrarily set the number of divisions of each divided region.

Third Embodiment

Reference will be made below to a third embodiment of the present invention. An endoscope system according to the third embodiment only differs in the configurations of the control unit of the control device and processing to be executed by the endoscope system. Specifically, in the third embodiment, only pixels in which the fluorescence is detected are subjected to exposure, and other pixels are exposed to visible light at a low gain. Thus, hereinafter, a configuration of the control unit of the endoscope system according to the third embodiment is described first, followed by processing to be executed by the endoscope system. In the third embodiment, the same reference signs are given to the same elements as in the above embodiments.

Figure 8A:
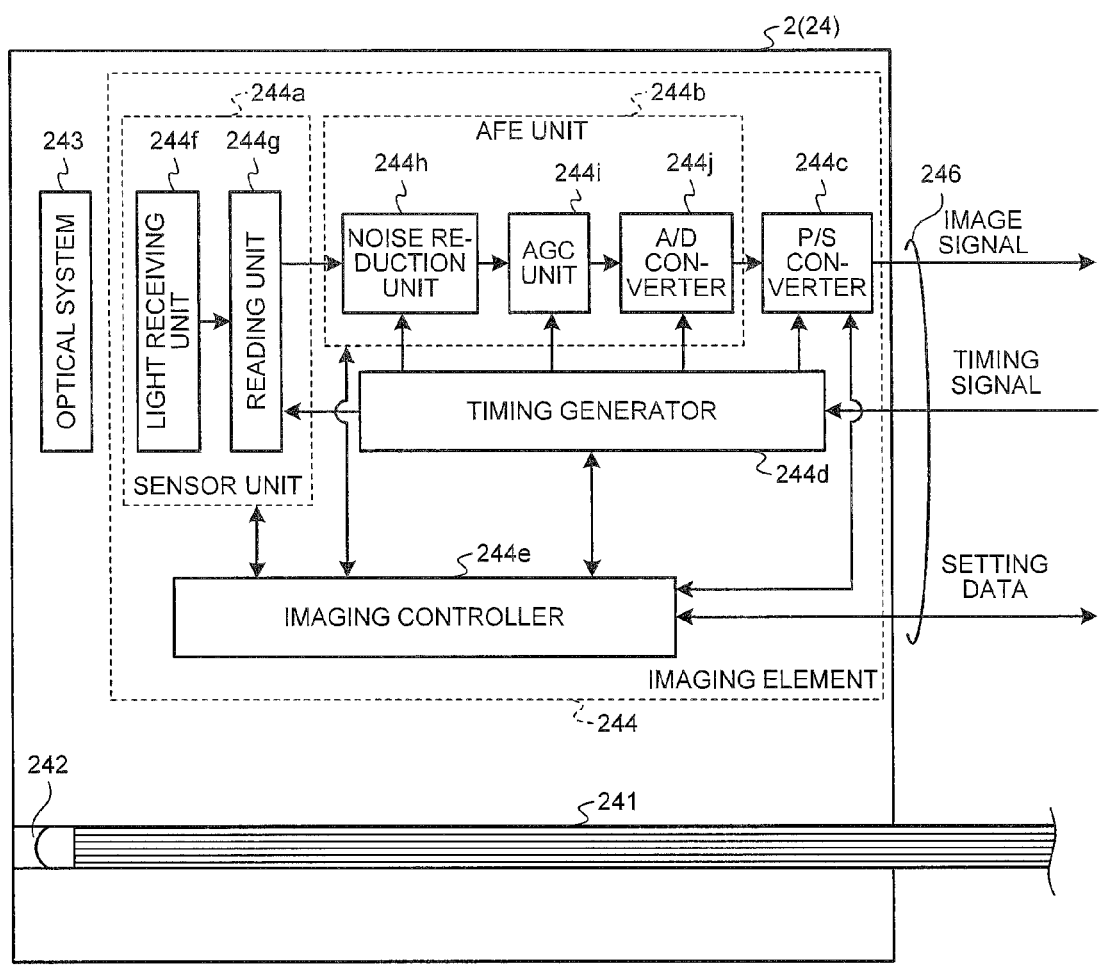
FIGS. 8A and 8B are a block diagram illustrating a functional configuration of a main part of an endoscope system according to a third embodiment of the present invention.
Figure 8B:
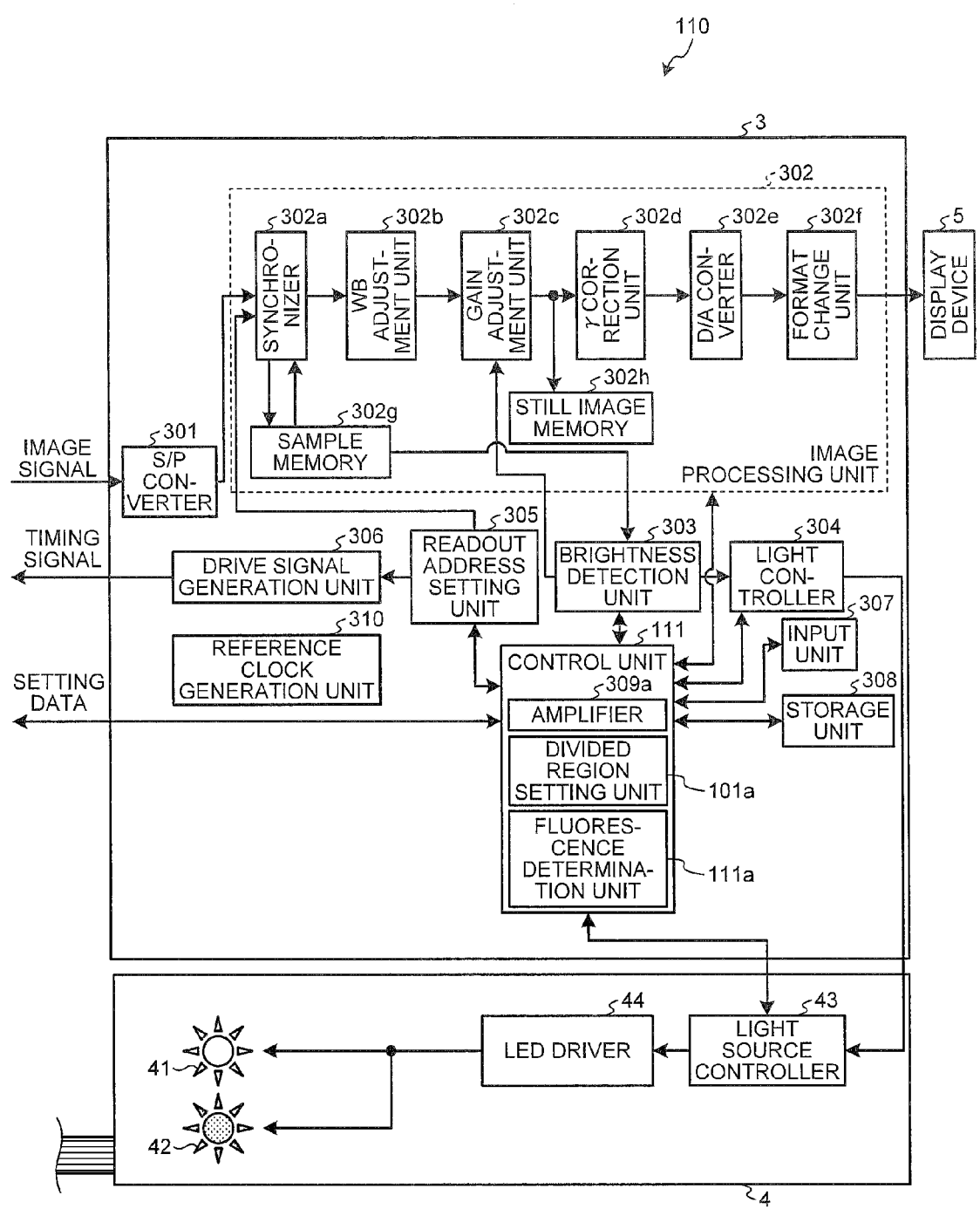

FIGS. 8A and 8B are a block diagram illustrating a functional configuration of a main part of an endoscope system 110 according to the third embodiment. As illustrated in FIG. 8B, a control device 3 of the endoscope system 110 includes a control unit 111.

The control unit 111 is configured by using a CPU and the like and performs drive control of components including the distal end section 24 and the light source device 4 and input and output control of information for the components. The control unit 111 transmits setting data for imaging control to the imaging controller 244e through a specified signal line included in the cable assembly 246. The control unit 111 includes an amplifier 309a, a divided region setting unit 101a, and a fluorescence determination unit 111a.

The fluorescence determination unit 111a determines presence or absence of a fluorescence region that emits the fluorescence in an image corresponding to the image signal generated by the imaging element 244. Specifically, the fluorescence determination unit 111a determines, upon the fluorescence observation, presence or absence of a region including a certain level of brightness in the image generated by the imaging element 244. The fluorescence determination unit 111a may determine an address of the pixel corresponding to the fluorescence region that emits the fluorescence in the image.

Figure 9:
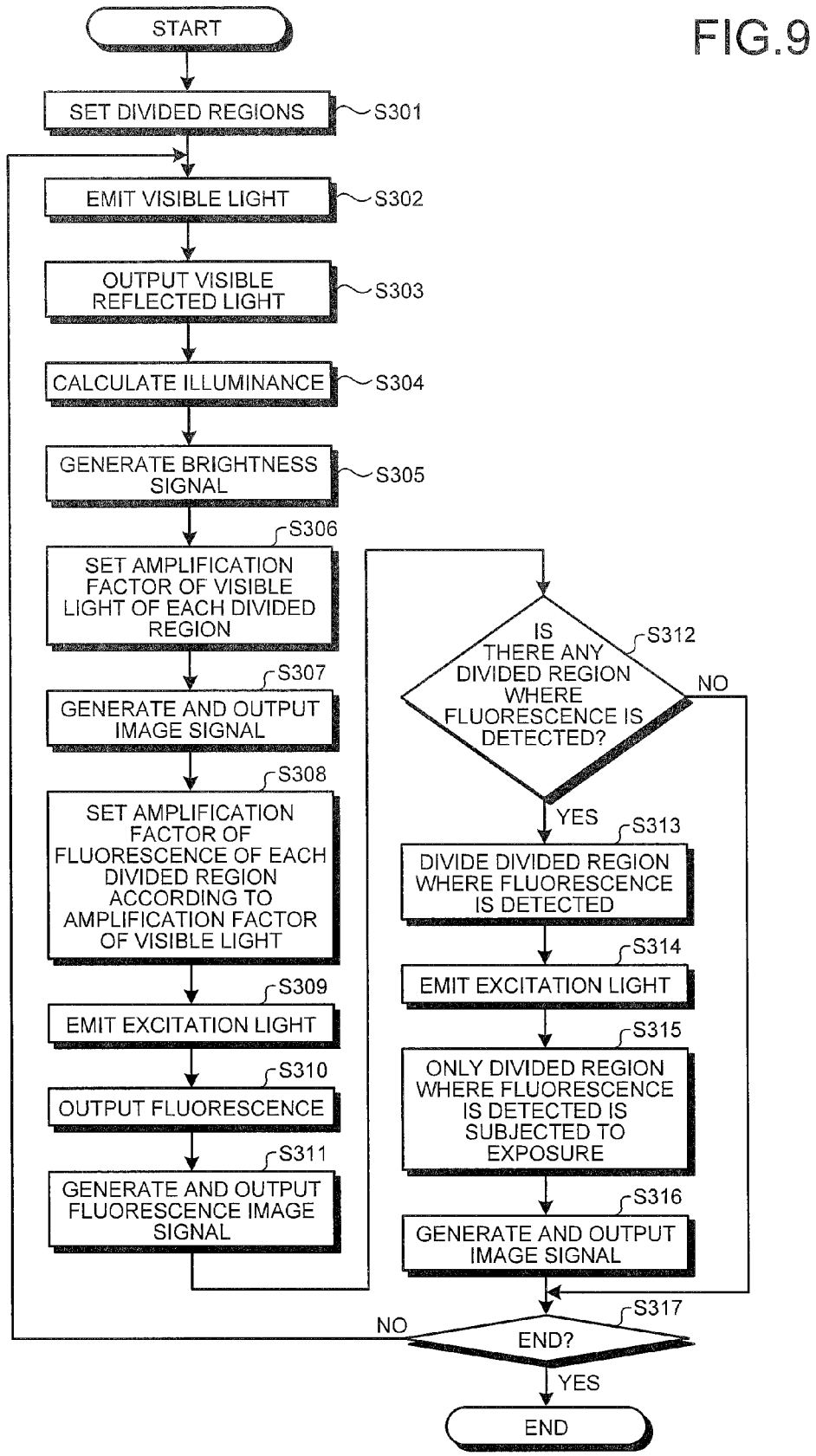
FIG. 9 is a flowchart illustrating an outline of processing that the endoscope system according to the third embodiment of the present invention executes.

Reference will be made below to processing to be executed by the endoscope system 110 having the above configuration. FIG. 9 is a flowchart illustrating an outline of processing that the endoscope system 110 according to the third embodiment executes.

As illustrated in FIG. 9, steps S301 to S308 correspond respectively to steps S201 to S207 and step S209 of FIG. 6. Further, steps S309 to S311 correspond respectively to steps S108 to S110 of FIG. 4.

After step S311, the fluorescence determination unit 111a determines whether or not there exists any divided region where the fluorescence is detected in the fluorescence image corresponding to the fluorescence image signal (step S312). Specifically, the fluorescence determination unit 111a determines whether or not a divided region including a certain level of brightness in the fluorescence image. When the fluorescence determination unit 111a determines that there exists any divided region where the fluorescence is detected in the fluorescence image corresponding to the fluorescence image signal (Yes in step S312), the endoscope system 1 shifts to step S313 to be described later. On the other hand, when the fluorescence determination unit 111a determines that there exists no divided region where the fluorescence is detected in the fluorescence image corresponding to the fluorescence image signal (No in step S312), the endoscope system 1 shifts to step S317 to be described later.

Figure 10:
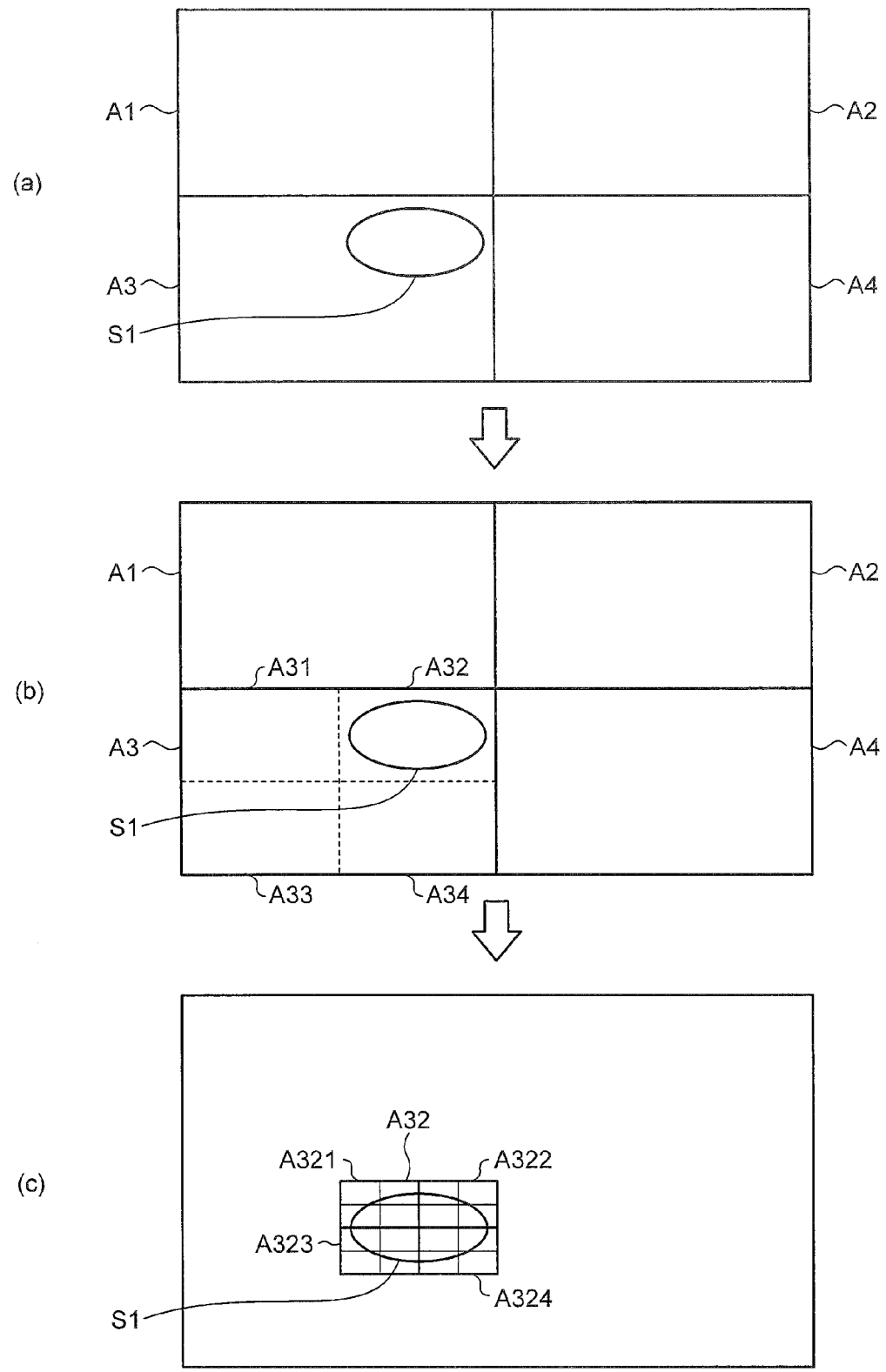
FIG. 10 is a view schematically illustrating divided regions obtained by division of an imaging surface performed by a divided region setting unit of FIG. 8B.

In step S313, the divided region setting unit 101a divides the divided region where the fluorescence is detected into predetermine regions to set small divided regions. Specifically, as illustrated in FIG. 10, the divided region setting unit 101a divides a divided region A3 where fluorescence S1 is detected into specified regions to set small divided regions A31 to A34 (FIG. 10: (a)→(b)). Subsequently, the divided region setting unit 101a sets, through the imaging controller 244e, a region of the light receiving unit 244f to be subjected to exposure. Specifically, the divided region setting unit 101a sets, through the imaging controller 244e, a region corresponding to the small divided region where the fluorescence S1 is detected as a region corresponding to the pixel of the light receiving unit 244f that receives the fluorescence for exposure.

Thereafter, the light source controller 43 drives the LED driver 44 under control of a control unit 111 to make the special-light light source 42 emit the excitation light (step S314), and amplifier 309a causes only the pixels constituting the small divided region set by the divided region setting unit 101a to receive the fluorescence for exposure (step S315). Thus, the sensor unit 244a only needs to expose only the pixel constituting the small divided region, enabling long-time exposure, which can increase the amplification factor (sensitivity) of the fluorescence. As a result, the endoscope system 1 exposes only the necessary pixels of the light receiving unit 244f for a long time to thereby allow the fluorescence image signal to be output continuously and smoothly as compared to a case where all the pixels constituting the light receiving unit 244f are subjected to long time exposure, without decreasing a set frame rate and without prolonging a time required to perform a series of imaging (exposure) operations.

Subsequently, the image processing unit 302 applies specified image processing to the image signal output from the imaging element 244 of the distal end section 24 to generate the fluorescence image signal and outputs the generated fluorescence image signal to the display device 5 (step S316).

Thereafter, the control unit 111 determines whether or not an end instruction signal has been input to the endoscope system 1 (step S317). When the control unit 111 determines that the end instruction signal has been input (Yes in S317), the endoscope system 1 ends this routine.

On the other hand, when the control unit 111 determines that the end instruction signal has not been input (No in S317), the endoscope system 1 returns to step S302. In this case, as illustrated in FIG. 10, the divided region setting unit 101a may further divide the small divided region where the fluorescence S1 is detected into specified regions until the end instruction signal is input to set minute divided regions A321 to A324 (FIG. 10: (b)→(c)), and then the amplifier 309a may set the amplification factor (sensitivity) for imaging of the fluorescence or long time exposure.

According to the third embodiment described above, the amplifier 309a causes only the pixels constituting the small divided region set by the divided region setting unit 101a to receive the fluorescence for exposure. Thus, the sensor unit 244a only needs to expose only the pixel constituting the small divided region, enabling long-time exposure, which can increase the amplification factor (sensitivity) of the fluorescence. As a result, the endoscope system 1 exposes only the necessary pixels of the light receiving unit 244f for a long time to thereby allow the fluorescence image signal to be output continuously and smoothly as compared to a case where all the pixels constituting the light receiving unit 244f are subjected to long time exposure, without decreasing a set frame rate and without prolonging a time required to perform a series of imaging (exposure) operations.

Further, in the third embodiment, a region where the fluorescence is detected by previous irradiation of the excitation light may be divided into specified regions to set the divided regions. That is, a configuration may be adopted in which high-sensitivity imaging is performed in a small region of interest. This allows the fluorescence image to be captured with a sufficient dynamic range or contrast.

Fourth Embodiment

Reference will be made below to a fourth embodiment. An endoscope system according to the fourth embodiment has the same configuration as those according to the above respective embodiments and only differs in processing to be executed by the endoscope system. Specifically, in the above embodiments, each pixel included in the divided region where the fluorescence is detected is subjected to exposure for a long time to increase imaging sensitivity of the fluorescence; on the other hand, in the fourth embodiment, a region where the amplification factor is increased is made gradually smaller from the entire region toward the region where the fluorescence is detected. Thus, hereinafter, processing to be executed by the endoscope system according to the fourth embodiment will be described. In the following description, the region where the fluorescence is detected is referred to as a region of interest (hereinafter, abbreviated as "ROI").

Figure 11:
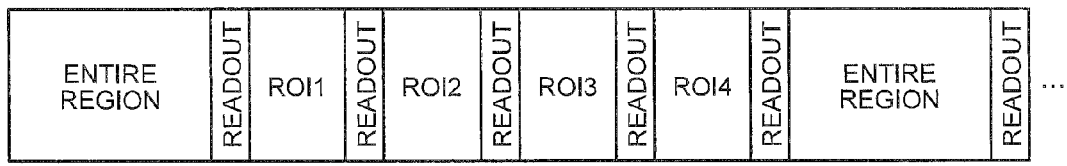
FIG. 11 is a time chart of processing to be executed by an endoscope system according to a fourth embodiment of the present invention.
Figure 11:

FIG. 11 is a time chart of processing to be executed by the endoscope system 1 according to the fourth embodiment. In FIG. 11, (a) of FIG. 11 illustrates a timing of regions to be output from the light receiving unit 244f, and (b) of FIG. 11 illustrates a timing at which reset is instructed for the pixels constituting the light receiving unit 244f. In FIG. 11, a horizontal axis indicates time.

Figure 12:
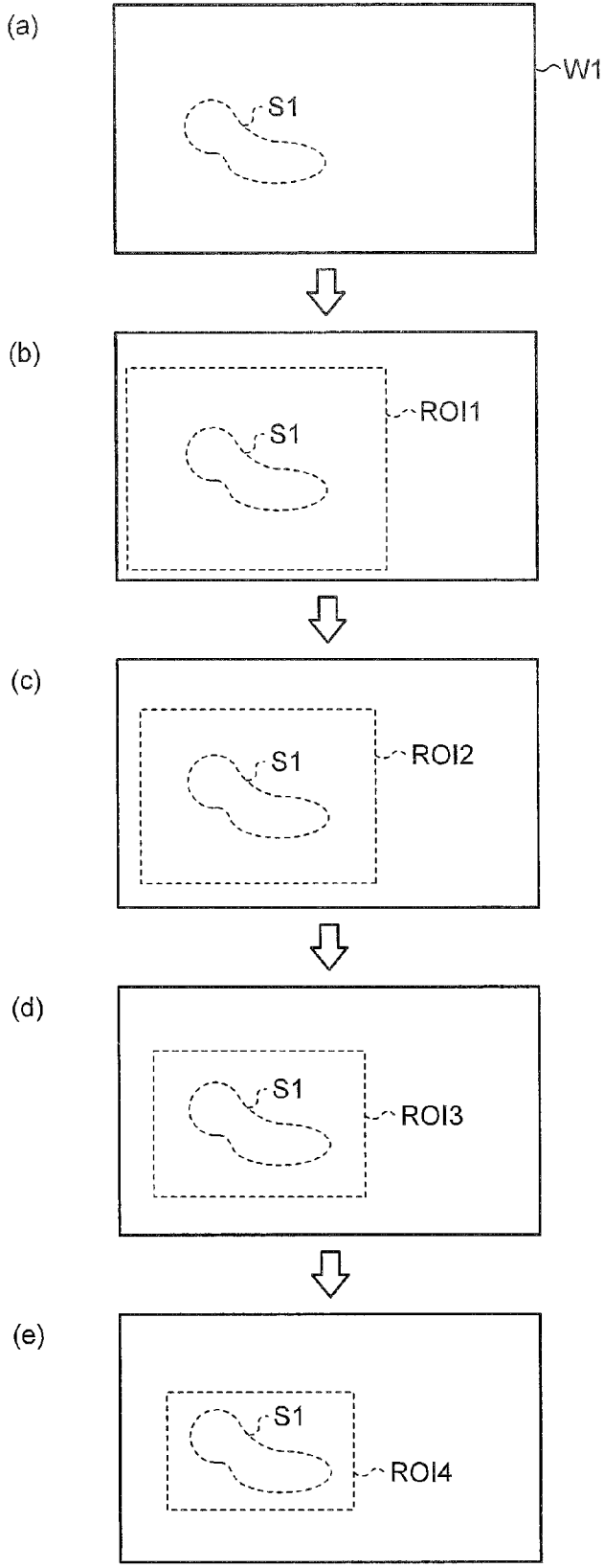
FIG. 12 is a view schematically illustrating divided regions obtained by division of an imaging surface performed by a divided region setting unit according to the fourth embodiment of the present invention.

As illustrated in FIG. 11, based on a determination result from the fluorescence determination unit 111a, the divided region setting unit 101a causes the imaging controller 244e to read out and output the regions of the light receiving unit 244f in the order of the entire region, ROI1, ROI2, ROI3, and ROI4. Specifically, as illustrated in FIG. 12, based on a determination result from the fluorescence determination unit 111a, the divided region setting unit 101a causes the imaging controller 244e to read out and output the regions of the light receiving unit 244f in the order of the entire region, R1, ROI1, ROI2, ROI3, and ROI4 such that the region where the fluorescence S1 corresponding to an affected part is detected becomes gradually smaller in an image W1. At this time, the images corresponding to the ROIs have the same center coordinates and sizes thereof are gradually reduced (ROI1>ROI2>ROI3>ROI4). As a result, the number of times of exposure becomes maximum at a superimposed portion of the ROIs, resulting in high sensitivity. However, the sensitivity is gradually decreased, eliminating feeling of difference from a surrounding image.

According to the fourth embodiment described above, based on a determination result from the fluorescence determination unit 111a, the divided region setting unit 101a makes a region of the light receiving surface of the light receiving unit 244f where the amplification factor is increased gradually smaller toward the region where the fluorescence S1 is detected. Thus, it is possible to obtain a smooth image in which the sensitivity is naturally increased without decreasing a frame rate of the imaging element 244.

Further, according to the fourth embodiment, the amplifier 309a sets, in a gradient manner, the sensitivity of a boundary of the region having the fluorescence, so that a feeling of strangeness of the image can be reduced.

Further, according to the fourth embodiment, even when there is any unnecessary high brightness region other than the ROI region, it is possible to reduce a region where the sensitivity is saturated and to prevent occurrence of malfunction, such as blackout, due to automatic control of brightness.

Fifth Embodiment

Reference will be made below to a fifth embodiment. In an endoscope system according to the fifth embodiment, two imaging elements are provided at the distal end section of the endoscope. Thus, hereinafter, only a configuration different from those of the endoscope systems according to the above respective embodiments will be described. In the fifth embodiment, the same reference sings are given to the same elements as in the above embodiments.

Figure 13:
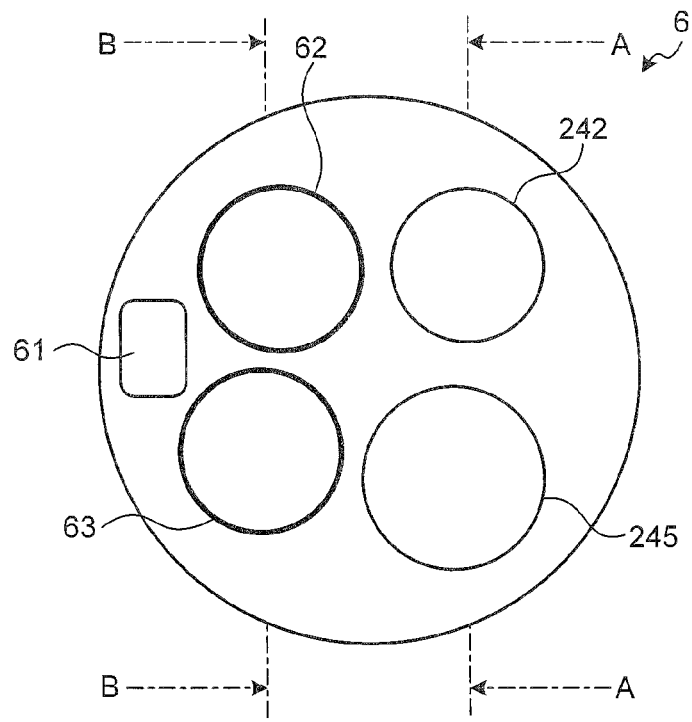
FIG. 13 is a view illustrating a distal end surface of a distal end section of an endoscope system according to a fifth embodiment of the present invention.
Figure 14:
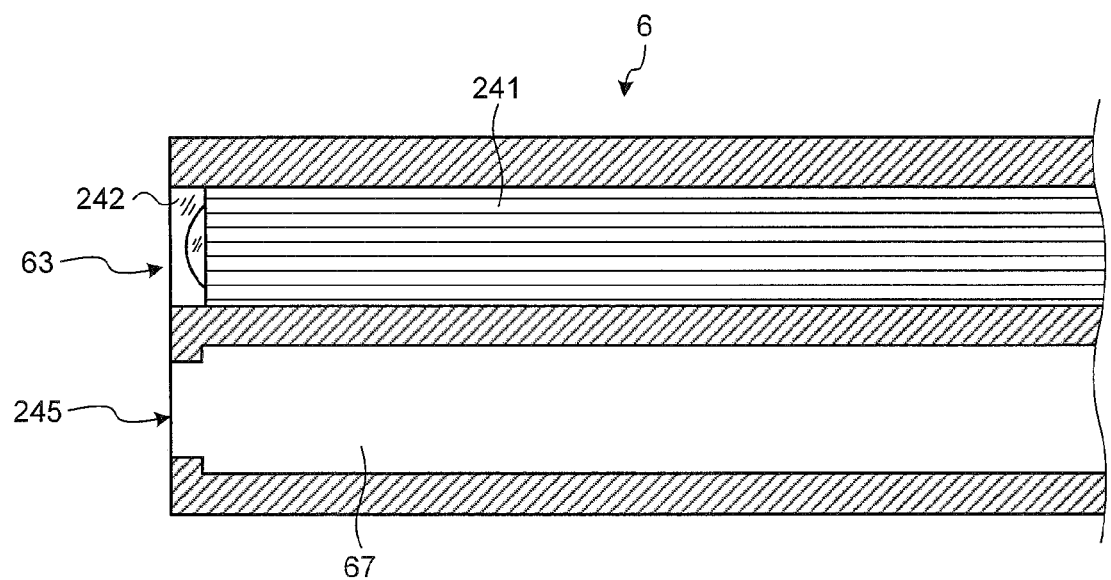
FIG. 14 is a view illustrating a part of a cut-out surface obtained by cutting the distal end section along a line A-A of FIG. 13.
Figure 15:
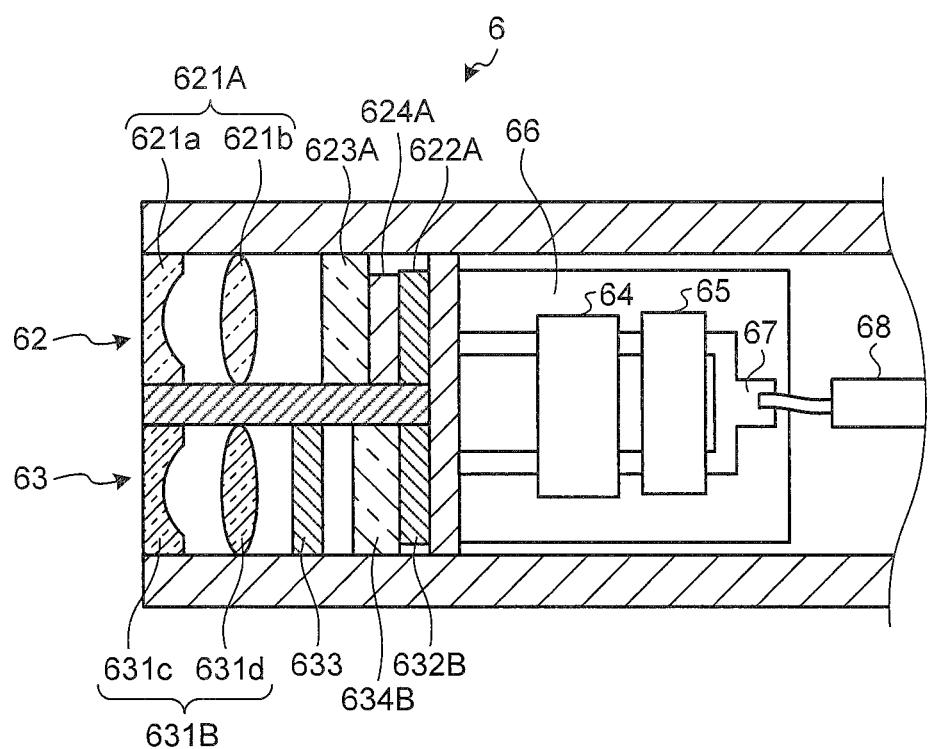
FIG. 15 is a view illustrating a part of a cut-out surface obtained by cutting the distal end section along a line B-B of FIG. 13.
Figure 16A:
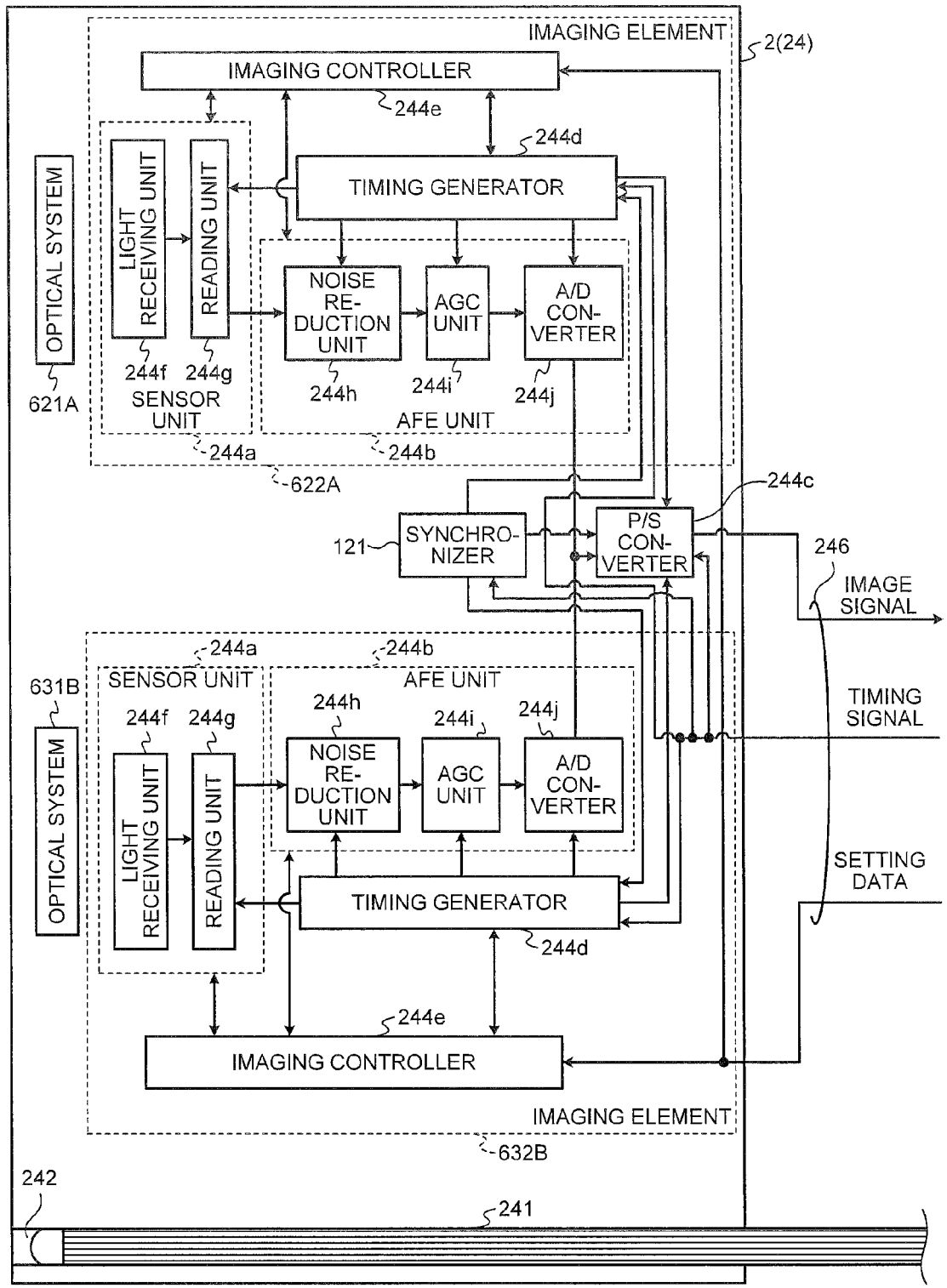
FIGS. 16A and 16B are a block diagram illustrating a functional configuration of a main part of the endoscope system according to the fifth embodiment of the present invention.
Figure 16B:
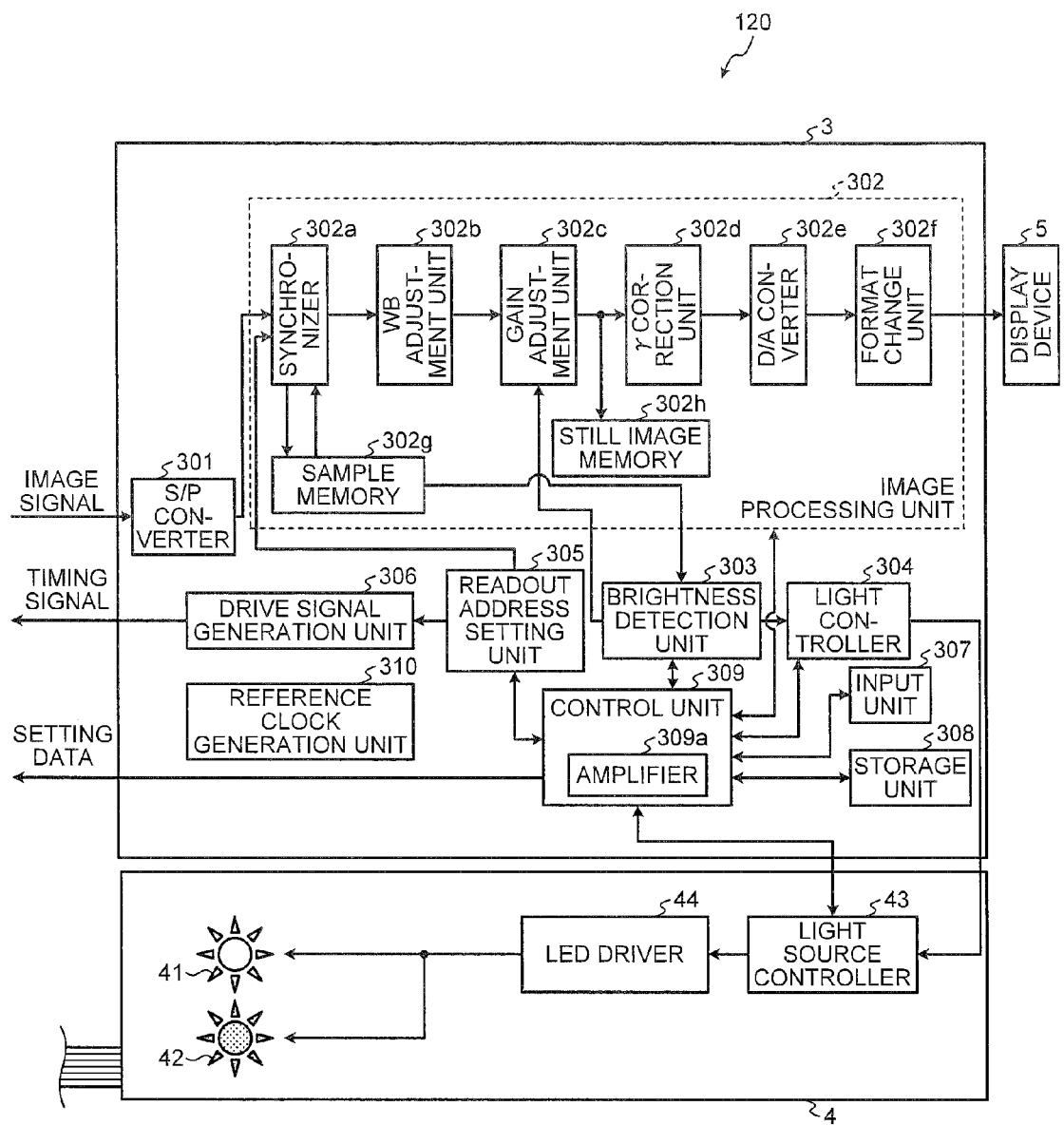

FIG. 13 is a view illustrating a distal end surface of a distal end section of the endoscope system according to the fifth embodiment. FIG. 14 is a view illustrating a part of a cut-out surface obtained by cutting the distal end section along a line A-A of FIG. 13. FIG. 15 is a view illustrating a part of a cut-out surface obtained by cutting the distal end section along a line B-B of FIG. 13. FIGS. 16A and 16B are a block diagram illustrating a functional configuration of a main part of the endoscope system according to the fifth embodiment.

As illustrated in FIGS. 13 to 16, in the distal end surface of a distal end section 6 of an endoscope 2, a washing nozzle 61, an observation window 62, an observation window 63, an illumination lens 242, and a treatment tool channel 245 are provided.

The observation windows 62 and 63 are closed. Light incident from outside to the observation window 62 is incident to a first optical system 621A constituted by a plurality of lenses 621a and 621b, collected, and incident to a first light receiving unit 622A. Light incident to the observation window 63 is incident to a second optical system 631B constituted by a plurality of lenses 631c and 631d, collected, and incident to a second light receiving unit 632B.

The first light receiving unit 622A has a plurality of imaging pixels arranged in a two-dimensional matrix and is disposed such that light emitted from the first optical system 621A is incident thereto. The first light receiving unit 622A receives light incident thereto through the first optical system 621A to capture a body cavity. A cover glass 623A is provided on a light receiving surface side of the first light receiving unit 622A. An on-chip filter 624A in which red (R), green (G), or blue (B) filters are arranged corresponding to an arrangement of pixels constituting the first light receiving unit 622A is provided between the cover glass 623A and first light receiving unit 622A, whereby the first light receiving unit 622A captures a color image. The on-chip filter 624A may be a complementary color filter in which cyan, magenta, yellow, and green filters are arranged.

The second light receiving unit 632B has a plurality of imaging pixels arranged in a two-dimensional matrix and is disposed such that light emitted from the second optical system 631B is incident thereto. A spectral filter 633 that transmits only light of a specified wavelength band and a cover glass 634B are provided on a light receiving surface side of the second light receiving unit 632B. The second light receiving unit 632B has characteristics of capturing an image for fluorescence observation corresponding to fluorescence of a specified wavelength band as a monochrome image.

The first light receiving unit 622A and second light receiving unit 632B are implemented on a circuit substrate 66 together with a driver 64 that instructs an imaging timing to the first light receiving unit 622A and second light receiving unit 632B and supplies power thereto, a conversion circuit 65 that reads out an image signal of the first light receiving unit 622A and second light receiving unit 632B and converts the image signal into an electric signal, and the like. The first and second light receiving units 622A and 632B are implemented on the circuit substrate 66 with their light receiving surfaces juxtaposed left and right. An electrode 67 is provided on the circuit substrate 66. The electrode 67 is connected to a signal line 68 for exchanging an electric signal with the control device 3 through, e.g., an anisotropic conductive resin film. A cable assembly is formed by a plurality of signal lines including a signal line 67a for transmitting an image signal which is an electric signal output from the first and second light receiving units 622A and 632B and a signal line for transmitting a control signal from the control device 3.

A synchronizer 121 sets pixels to be read out from the first and second light receiving units 622A and 632B such that first and second light receiving units 622A and 632B alternately read out image information. The synchronizer 121 controls timings of exposure processing performed in the first and second light receiving units 622A and 632B and pixel information readout processing from the first and second light receiving units 622A and 632B by the timing generator 244d and AFE unit 244b in correlation with each other. The pixel information read out from the first and second light receiving units 622A and 632B is transmitted by the same transmission path.

In an endoscope system 120 thus configured, the brightness detection unit 303 generates the brightness signal based on the image signal captured by the first light receiving unit 622A, and the amplifier 309a sets, based on the amplification factor according to the brightness signal generated by the brightness detection unit 303, the amplification factor of the image signal that the second light receiving unit 632B generates under irradiation with the excitation light. This allows the endoscope system 120 to substantially simultaneously adjust sensitivity of imaging of the excitation light with imaging operation of the normal light (visible light).

According to some embodiments, based on the amplification factor according to the brightness signal of the image signal generated by the imaging element under irradiation with the normal light, the brightness signal being generated by the brightness signal generation unit, the amplifier sets the amplification factor of the fluorescence of each pixel. This allows observation of the fluorescence image to be adequately performed without overlooking emitted fluorescence.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus comprising:
   an excitation light emission unit configured to irradiate a subject with excitation light for exciting a fluorescent substance introduced into the subject;
   a normal light emission unit configured to irradiate the subject with normal light including a visible wavelength range different from the excitation light;
   an imaging unit configured to form an optical image of the subject irradiated with the excitation light or normal light on an imaging surface to generate an image signal;
   a brightness signal generation unit configured to generate a brightness signal indicating brightness, based on the image signal generated by the imaging unit under irradiation with the normal light;
   an amplification unit configured to set an amplification factor of the image signal to be generated by the imaging unit under irradiation with the excitation light, based on an amplification factor of the image signal according to the brightness signal generated by the brightness signal generation unit;
   a divided region setting unit configured to divide the imaging surface to set a plurality of divided regions; and
   a fluorescence determination unit configured to determine presence or absence of a fluorescence region that emits fluorescence in a fluorescence image corresponding to the image signal generated under irradiation with the excitation light,
   wherein the brightness signal generation unit is configured to generate brightness signals of the plurality of divided regions set by the divided region setting unit,
   wherein based on an amplification factor according to each of the brightness signals, the amplification unit is configured to set an amplification factor of the image signal corresponding to each of the divided regions under irradiation with the excitation light, wherein when the fluorescence determination unit determines that there is the fluorescence region in the fluorescence image, the divided region setting unit divides the divided region including the fluorescence region to set a plurality of small divided regions, and wherein based on the amplification factor according to each of the brightness signals, the amplification unit is configured to set an amplification factor of the image signal corresponding to each of the small divided regions under irradiation with the excitation light.

2. The imaging apparatus according to claim 1, wherein the amplification unit is configured to set the amplification factor of the image signal based on a gain.

3. The imaging apparatus according to claim 1, wherein the amplification unit is configured to set the amplification factor of the image signal based on an exposure time.

4. The imaging apparatus according to claim 1, wherein the divided region setting unit is configured to divide each of the divided regions to set a plurality of small divided regions, and wherein based on the amplification factor according to each of the brightness signals, the amplification unit is configured to set an amplification factor of the image signal corresponding to each of the small divided regions under irradiation with the excitation light.

5. An imaging apparatus comprising:

an excitation light emission unit configured to irradiate a subject with excitation light for exciting a fluorescent substance introduced into the subject;

a normal light emission unit configured to irradiate the subject with normal light including a visible wavelength range different from the excitation light;

an imaging unit configured to form an optical image of the subject irradiated with the excitation light or normal light on an imaging surface to generate an image signal;

a brightness signal generation unit configured to generate a brightness signal indicating brightness, based on the image signal generated by the imaging unit under irradiation with the normal light;

an amplification unit configured to set an amplification factor of the image signal to be generated by the imaging unit under irradiation with the excitation light, based on an amplification factor of the image signal according to the brightness signal generated by the brightness signal generation unit;

a divided region setting unit configured to divide the imaging surface to set a plurality of divided regions; and a fluorescence determination unit configured to determine presence or absence of a fluorescence region that emits fluorescence in a fluorescence image corresponding to the image signal generated under irradiation with the excitation light, wherein the brightness signal generation unit is configured to generate brightness signals of the plurality of divided regions set by the divided region setting unit, wherein based on an amplification factor according to each of the brightness signals, the amplification unit is configured to set an amplification factor of the image signal corresponding to each of the divided regions under irradiation with the excitation light, and wherein when the fluorescence determination unit determines that there is the fluorescence region in the fluorescence image, the divided region setting unit makes the divided region including the fluorescence region smaller with lapse of time.

6. The imaging apparatus according to claim 5, wherein the amplification unit is configured to set the amplification factor of the image signal based on a gain.

7. The imaging apparatus according to claim 5, wherein the amplification unit is configured to set the amplification factor of the image signal based on an exposure time.

8. The imaging apparatus according to claim 5, wherein the divided region setting unit is configured to divide each of the divided regions to set a plurality of small divided regions, and wherein based on the amplification factor according to each of the brightness signals, the amplification unit is configured to set an amplification factor of the image signal corresponding to each of the small divided regions under irradiation with the excitation light.

* * * * *